United States Patent
Sels et al.

(10) Patent No.: US 11,414,519 B2
(45) Date of Patent: Aug. 16, 2022

(54) ORTHO ALKOXY BISPHENOL MONOMERS

(71) Applicant: KATHOLIEKE UNIVERSITEIT LEUVEN, Leuven (BE)

(72) Inventors: Bert Sels, Westerlo (BE); Steven-Friso Koelewijn, Kessel-Lo (BE)

(73) Assignee: KATHOLIEKE UNIVERSITEIT LEUVEN, Leuven (BE)

( * ) Notice: Subject to any disclaimer, the term of this patent is extended or adjusted under 35 U.S.C. 154(b) by 415 days.

(21) Appl. No.: 16/627,054

(22) PCT Filed: Jun. 28, 2018

(86) PCT No.: PCT/EP2018/067480
§ 371 (c)(1),
(2) Date: Dec. 27, 2019

(87) PCT Pub. No.: WO2019/002503
PCT Pub. Date: Jan. 3, 2019

(65) Prior Publication Data
US 2020/0123315 A1    Apr. 23, 2020

(30) Foreign Application Priority Data

Jun. 29, 2017 (GB) .................................. 1710436

(51) Int. Cl.
| C08G 63/672 | (2006.01) |
| B01J 29/08 | (2006.01) |
| B01J 29/18 | (2006.01) |
| B01J 29/70 | (2006.01) |
| C07C 39/16 | (2006.01) |
| C08G 64/30 | (2006.01) |

(52) U.S. Cl.
CPC ............ *C08G 63/672* (2013.01); *B01J 29/08* (2013.01); *B01J 29/18* (2013.01); *B01J 29/7007* (2013.01); *C07C 39/16* (2013.01); *C08G 64/307* (2013.01)

(58) Field of Classification Search
CPC .... C08G 63/193; C08G 63/672; C08G 64/06; C08G 64/24; C08G 64/307; C07C 39/16; C07C 41/30; C07C 67/347; B01J 29/08; B01J 29/18; B01J 29/7007
See application file for complete search history.

(56) References Cited

U.S. PATENT DOCUMENTS 9,120,893 B1    9/2015 Chandra et al.

FOREIGN PATENT DOCUMENTS

| EP | 0676387 A1 | 10/1995 |
| JP | 2000239206 A | 9/2000 |
| WO | 2015168225 A2 | 11/2015 |

OTHER PUBLICATIONS

Office Action from corresponding EP Application No. 18737554.8, dated Jan. 27, 2021.
(Continued)

*Primary Examiner* — Brian A McCaig
(74) *Attorney, Agent, or Firm* — Workman Nydegger

(57) ABSTRACT

A process for making ortho alkoxy bisphenol monomers includes contacting an (alk-1-enyl)alkoxyphenol (type 1) with an alkoxyphenol (type 2) in the presence of an acidic catalyst. Both type of renewable phenols (type 1 and 2) can be generated from lignocellulosic biomass. The use of such alkoxy phenols as a precursor to bisphenol monomers has the potential to reduce the cost and environmental impact of structural materials, while meeting or exceeding the performance of current petroleum-derived polymers, such as thermoplastics and thermoset resins.

30 Claims, 5 Drawing Sheets

(56) References Cited

OTHER PUBLICATIONS

Dodds et al., "Molecular Structure in Relation to Oestrogenic Activity. Compounds without a Phenanthrene Nucleus," Proceedings of The Royal Society of London, Series B, Biological Sciences, vol. 125, Apr. 27, 1938, pp. 222-232.
Engelhardt et al., "Summary of Structural Information Available from the Spectra," High-Resolution Solid-State NMR of Silicates and Zeolites, 1987, pp. 145-157.
Klinowski, "Recent Advances in Solid-State NMR of Zeolites," Annual Review of Materials Science, vol. 18, 1988, pp. 189-218.
Cichocki et al., "Synthesis and Characterization of Boralites with the MFI Structure," Zeolites, vol. 10, Jul./Aug. 1990, pp. 577-582.
Krishnan et al., "Bisphenol-A: An Estrogenic Substance is Released from Polycarbonate Flasks during Autoclaving," The Endocrine Society, vol. 132, No. 6, 1993, pp. 2279-2286.
Brotons et al., "Xenoestrogens Released from Lacquer Coatings in Food Cans," Environmental Health Perspectives, vol. 103, 1995, pp. 608-612.
On et al., "Titanium Boralites with MFI Structure Characterized Using XRD, XANES, IR, and UV-Visible Techniques: Effect of Hydrogen Peroxide on the Preparation," Academic Press: Journal of Catalysis, vol. 157, Jul. 28, 1995, pp. 235-243.
On et al., "Titanium Boralites with MFI Structure Characterized using XRD, IR, UV-Vis XANES and MAS-NMR Techniques," Elesevier Science B.V., 1995, pp. 535-541.
Remy et al., "Dealuminated H-Y Zeolites: Relation Between Physicochemical Properties and Catalytic Activity in Heptane and Decane Isomerization," Journal of Physical Chemistry, vol. 100, Feb. 27, 1996, pp. 12440-12447.
Olea et al., "Estrogenicity of Resin-Based Composites and Sealants Used in Dentistry," Environmental Health Perspectives, vol. 104, No. 3, Mar. 1996, pp. 298-305.
Storck et al., "Characterization of Micro- and Mesoporous Solids by Physisorption Methods and Pore-Size Analysis," Applied Catalysis A: General, vol. 174, May 12, 1998, pp. 137-146.
Rouquerol et al., "Adsorption by Powders and Porous Solids: Principles, Methodology and Applications," Academic Press, 1999, pp. 1-467.
Weitkamp, "Zeolites and Catalysis," Solid State Ionics, vol. 131, Dec. 15, 1999, pp. 175-188.
Groen et al., "Pore Size Determination in Modified Micro- and Mesoporous Materials. Pitfalls and Limitations in Gas Adsorption Data Analysis," Microporous and Mesoporous Materials, vol. 60, Mar. 28, 2003, pp. 1-17.
Baerlocher et al., "Atlas of Zeolite Framework Types," Structure Commission of the International Zeolite Association, Sixth Edition, 2007, pp. i-398.
Ertl et al., "Handbook of Heterogenous Catalysis," Wiley-VCH Verlag GmbH& Co., Second Edition, vol. 1, 2008, pp. 1-3865.
Biedermann et al., "Transfer of Bisphenol A from Thermal Printer Paper to the Skin," vol. 398, No. 1, Analytical and Bioanalytical Chemistry, Jul. 11, 2010, pp. 571-576.
"StandardTest Methods for Determining the Biobased Content of Solid, Liquid, and Gaseous Samples Using Radiocarbon Analysis," ASTM International, Designation: D6866-12, May 2012, 14 Pages.
Galkin et al., "Selective Route to 2-Propenyl Aryls Directly from Wood by a Tandem Organosolv and Palladium-Catalysed Transfer Hydrogenolysis," ChemSusChem, vol. 7, 2014, pp. 2154-2158.
Luo et al., "Total Utilization of Miscanthus Biomass, Lignin and Carbohydrates, Using Earth Abundant Nickel Catalyst," ACS Sustainable Chemistry & Engineering, Jan. 29, 2016, 7 Pages.
Anderson et al., "Reductive Catalytic Fractionation of Corn Stover Lignin," ACS Sustainable Chemistry & Engineering, Sep. 3, 2016, 15 Pages.
Galkin et al., "Hydrogen-Free Catalytic Fractionation of Woody Biomass," ChemSusChem, vol. 9, 2016, pp. 1-9.
Jastrzebski et al., "Tandem Catalytic Depolymerization of Lignin by Water-Tolerant Lewis Acids and Rhodium Complexes," ChemSusChem, vol. 9, 2016, pp. 1-7.
Mintova et al., "Verified Syntheses of Zeolitic Materials," Synthesis Commission of the International Zeolite Association, Third Edition, 2016, 410 Pages.
Search Report from GB Application No. GB1710436.5, dated Sep. 3, 2017.
International Preliminary Report on Patentability and Written Opinion from PCT Application No. PCT/EP2018/067480, dated Sep. 19, 2019.
International Search Report and Written Opinion from PCT Application No. PCT/EP2018/067480, dated Oct. 11, 2018.
Findik, et al., "Isoeugenol-based novel potent antioxidants: Synthesis and reactivity," European Journal of Medicinal Chemistry, vol. 46, Jul. 28, 2011, pp. 4618-4624.
Office Action from corresponding Chinese Patent Application No. 201880043659.1, dated Apr. 18, 2022.

ORTHO ALKOXY BISPHENOL MONOMERS

FIELD OF INVENTION

The invention relates in general to a process for making ortho alkoxy bisphenol monomers from (alpha-alkenyl) alkoxyphenols and uses thereof and more particularly to a process for preparing ortho alkoxy bisphenol monomers, which may be used as starting products for the preparation of (bio)polymers, such as thermoplastics and thermoset resins.

BACKGROUND OF THE INVENTION

Bisphenols are useful bifunctional aromatic compounds that can be polymerized into polymeric materials. Such polymeric materials are useful in the preparation of commodity, engineering and high-performance thermoplastic materials characterized by outstanding mechanical, optical, electronic and thermal properties. Bisphenols are also useful in the preparation of thermoset plastics applications as coatings, adhesives and additives, such as antioxidants, plasticizing agents, anticorrosive agents and flame retardants.

Bisphenols are usually prepared by condensing (short-chain) ketones or aldehydes, such as acetone, formaldehyde and acetaldehyde, with phenol under mild conditions using Brønsted acid catalysts in the absence of solvents. The efficiency of this catalytic reaction is hindered by (i) regioselectivity issues, (ii) aldol condensation and (iii) acid-catalyzed isomerization. In order to give the final polymers the desired physicochemical properties such as color stability, crystallinity, and intermolecular attractive forces between the polymer chains, the synthesis requires a high regioselectivity towards the desired p,p'-isomer. Still, the unselective formation of undesired o,p' and o,o'-isomers, which is a common isomeric complication in electrophilic aromatic substitution reactions, remains. In the case of BPA synthesis most of the commercial applications require separation of the isomers by energy-intensive procedures involving fractional distillation coupled with crystallization. Industrially, a higher p,p'-regioselectivity is therefore obtained via cooperative acid-thiol catalysis through addition of (in)soluble sulphur-containing cocatalysts, which favor the para addition to the first phenol, but do not influence the second phenol addition or parallel acid-catalyzed isomerization. Additionally, regioselectivity can be manipulated through the presence or absence of water during synthesis. Removing condensation water during the reaction favors p,p'-connectivity, while adding water and/or minimizing the loss of water favors non-p,p' connectivity. The negative effect of water is typically avoided by working in an excess of phenol, which simultaneously reduces formation of aldol condensation products, or by using an azeotropic solvent, for example toluene and xylenes, to aid in water removal. In order to avoid the influence of the acid-catalyzed isomerization one usually operates at low conversions and/or short contact times.

Nonetheless, bisphenols such as BPA, are (long-known) endocrine disruptors and responsible for displacement of natural estradiol from estrogen receptors by mimicking the natural hormone (Dodds and Lawson, *Proc. R. Soc. Lond. B*, 1938, 125, 222-232). Although BPA-derived polymers such as polycarbonates are extremely stable and virtually non-degradable under physiological conditions various studies indicate that bisphenols are released into the environment from autoclaving polycarbonate flasks (Krishnan et al., *Endocrinology*, 1993, 132(6), 2279-2286) and epoxy resin lining in food cans (Brotons et al., *Environ. Health Persp.*, 1995, 103(6), 608), leaching from resin-based composites/sealants in dentistry (Olea et al., *Environ. Health Persp.*, 1996, 104(3), 298-305) and dermal absorption from thermal receipt printer paper (Biedermann et al., *Anal. Bioanal. Chem.*, 2010, 398(1), 571-576). Therefore, numerous studies couple a (low dose) exposure to BPA during fetal development and puberty to, among other, lifelong physical and mental health effects such as birth defects, obesity, thyroid issues and changes in reproductive development. It is estimated that over 90% of the population of industrial countries have BPA and its metabolites in their urine.

Besides its controversial status regarding health and the environment, (more frequent) petro-aromatic shortages further stress the need to replace the petroleum-derived phenol precursor by sustainable renewable phenolics. Commercially available bisphenols, especially polyaromatic bisphenols, currently originate from benzene-derived phenol (via the Hock-process), which is a non-renewable resource on the time scale of consumption. However, in order to substantially replace the bulk chemical BPA by renewable resources, it is crucial that these molecules are abundantly and economically available. Hereto renewable sources of aromaticity, such as lignin, the third most abundant natural polymer, which is rich in aromatic content, hold the potential to be a low cost sustainable alternative to petro-aromatic feedstocks. Valorization of chemically (un)altered lignin into monophenolics through oxidative, reductive, redox-neutral (acidic, alkaline, solvolytic and thermal) and biocatalytic routes provides an auspicious feedstock of sustainable alternative phenolics. A very promising route for high-yield lignin depolymerization is redox-neutral catalytic fractionation, resulting in high yields of unsaturated (alk-1-enyl)guaiacols and -syringols (Galkin et al., *ChemSusChem*, 2014, 7(8), 2154-2158; Galkin et al., ChemSusChem, 2016, 9(23), 3280-3287; Anderson et al., *ACS Sustain. Chem. Eng.*, 2016, 4(12), 6940-6950; Luo et al., *ACS Sustain. Chem. Eng.*, 4(4), 2316-2322; Jastrzebski et al., *ChemSusChem*, 2016, 9(16), 2074-2079).

Favorable bisphenol alternatives therefore preferably (i) originate from an environmentally benign synthesis, (ii) are derived from sustainable renewable phenolics, (iii) must provide comparable or improved physicochemical properties, (iv) entail less or no negative health effects and (v) preferably function as a drop-in replacement. Many current alternatives provide similar properties but are difficult to synthesize an require expensive processing steps. These intensive synthesis steps limit their application as industrial alternatives to bisphenols. Other alternatives are derived from natural resources; however, these resources cannot sustain the production quotas necessary for industrial production. Furthermore, many other bisphenol alternatives are still synthesized with and/or from toxic or volatile molecules such as sulphur-containing co-catalysts, formaldehyde, acetaldehyde, propionaldehyde and acetone. Additionally, many synthesis use electrochemistry, harsh mineral acids, or complex catalyst systems for the synthesis of bisphenol alternatives, which may lead to low yields, damaged processing equipment, and high catalyst cost. Moreover, when it concerns separation and purification, it would be advantageous if no (condensation) water would be released in the reaction mixture.

Therefore, there remains a need for processes for preparing bisphenol alternatives that overcome one or more of the aforementioned issues (i.e., regioselectivity, aldol condensation, condensation water, endocrine activity and renewability). It is an object of the present invention to provide a process for preparing sustainable bisphenol alternatives.

SUMMARY OF THE INVENTION

The present inventors have now surprisingly found that one or more of these objects can be obtained by the process of the present invention.

The present invention concerns a process for making ortho alkoxy bisphenol monomers, comprising the step of contacting at least one (alk-1-enyl)alkoxyphenol; wherein said (alk-1-enyl)alkoxyphenol is an 3-(alk-1-enyl)alkoxyphenol, 4-(alk-1-enyl)alkoxyphenol, an 5-(alk-1-enyl) alkoxyphenol or an 6-(alk-1-enyl)alkoxyphenol;
comprising the step of contacting at least one alkoxyphenol; wherein said alkoxyphenol is a 2-alkoxyphenol, a 3-alkoxyphenol, a 2,3-dialkoxyphenol, or a 2,6-dialkoxyphenol;
with at least one acidic catalyst; wherein said acidic catalyst comprises a soluble acid, an acidic ion-exchange resin, an acidic clay or an acidic zeolite.

The independent and dependent claims set out particular and preferred features of the invention. Features from the dependent claims may be combined with features of the independent or other dependent claims appropriate.

The above and other characteristics, features and advantages of the present invention will become apparent from the following detailed description, which illustrates, by way of example, the principle of the invention.

It will be apparent to those skilled in the art that various modifications and variations can be made in the present disclosure without departing from the scope or spirit of the disclosure. Other aspects of the disclosure will be apparent to those skilled in the art from consideration of the specifications and practice of the disclosure disclosed herein. It is intended that the specification and examples be considered as exemplary only, with a true scope and spirit of the disclosure being indicated by the following claims.

BRIEF DESCRIPTION OF THE FIGURES

The accompanying figures, which are incorporated in and constitute a part of this specification, illustrate several aspects and together with the description serve to explain the principles of the invention.

DETAILED DESCRIPTION OF THE INVENTION

Figure 1:
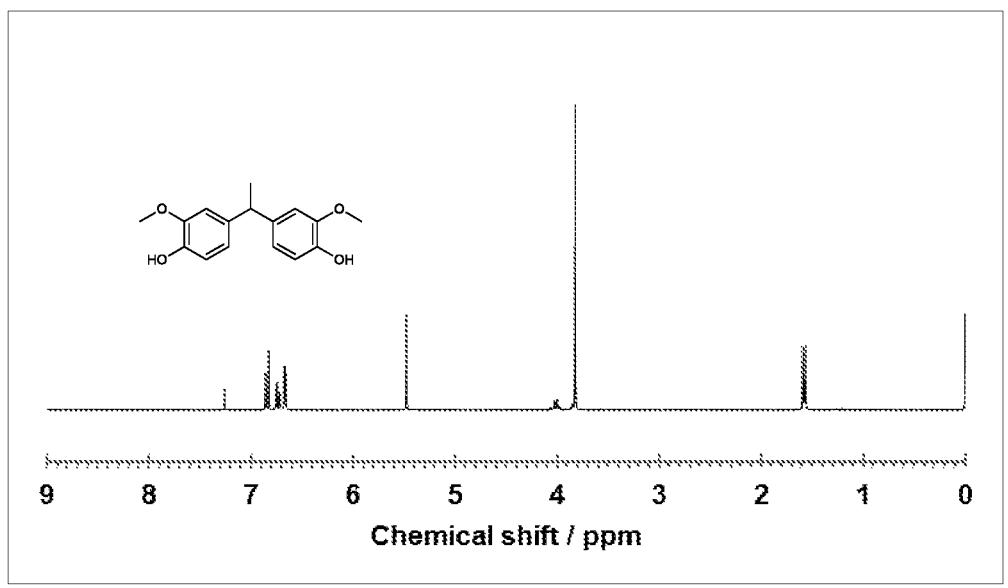
FIG. 1 shows a representative $^1$H NMR spectrum of GGE monomer prepared according to the present invention.

The present invention can be understood more readily by reference to the following detailed description of the invention and the examples included therein.

Before the present compounds, compositions, articles, systems, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of aspects described in the specification.

All publications mentioned herein are incorporated herein by reference to disclose and describe the methods and/or materials in connection with which the publications are cited.

A. DEFINITIONS

Unless defined otherwise, all technical and scientific terms used herein have the same meaning as commonly understood by one of ordinary skill in the art to which this invention belongs. By means of further guidance, definitions for the terms used in the description are included to better appreciate the teaching of the present invention. The terms or definitions used are to be construed in accordance with the following definitions, unless a context dictates otherwise.

As used herein, the singular forms "a," "an" and "the" include both singular and plural referents unless the context clearly dictates otherwise.

It is also to be understood that the terminology used herein is for the purpose of describing particular aspects only and is not intended to be limiting. As used herein, the terms "comprising", "comprises" and "comprised of" are synonymous with "including", "includes" or "containing", "contains", and are inclusive or open-ended and do not exclude additional, non-recited members, elements or method steps. The terms "comprising", "comprises" and "comprised of" also include the term "consisting of" and "consisting essentially of".

As used herein, the terms "combination" is inclusive of blends, mixtures, alloys, reaction products, and the like.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Ranges can be expressed herein as from one particular value, and/or to another particular value. When such a range is expressed, another aspect includes from the one particular value and/or to the other particular value. Similarly, when values are expressed as approximations, by use of the antecedent 'about,' it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art.

In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

As used herein, the terms "optional" or "optionally" means that the subsequently described event or circumstance can or cannot occur, and that the description includes instances where said event or circumstance occurs and instances where it does not. For example, the phrase "optionally substituted alkyl" means that the alkyl group can or cannot be substituted and that the description includes both substituted and unsubstituted alkyl groups.

As used herein, the term "effective amount" refers to an amount that is sufficient to achieve the desired modification of a physical property of the composition or material. For example, an "effective amount" of a filler refers to an amount that is sufficient to achieve the desired improvement in the property modulated by the formulation component, e.g., achieving the desired level of modulus. The specific level in terms of wt % in a composition required as an effective amount will depend upon a variety of factors including the amount and type of polycarbonates, amount and type of thermally conductive filler, and use of the article made using the composition.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the disclosure. Thus, if there are a variety of additional steps that can be performed it is understood that each of these additional steps can be performed with any specific aspect or combination of aspects of the methods of the disclosure.

References in the specification and concluding claims to parts by weight of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

As used herein the terms "weight percent", "wt %," and "wt. %", which can be used interchangeably, indicate the percent by weight of a given component based on the total weight of the composition, unless otherwise specified. That is, unless otherwise specified, all wt % values are based on the total weight of the composition. It should be understood that the sum of wt % values for all components in a disclosed composition or formulation are equal to 100.

Compounds are described using standard nomenclature. For example, any position not substituted by any indicated group is understood to have its valence filled by a bond as indicated, or a hydrogen atom. A dash ("-") that is not between two letters or symbols is used to indicate a point of attachment for a substituent. For example, —CHO is attached through carbon of the carbonyl group. Unless defined otherwise, technical and scientific terms used herein have the same meaning as is commonly understood by one of skill in the art to which this disclosure belongs.

As used herein, "polycarbonate" refers to an oligomer or polymer comprising residues of one or more dihydroxy compounds, e.g., dihydroxy aromatic compounds, joined by carbonate linkages; it also encompasses homopolycarbonates, copolycarbonates and (co)polyester carbonates.

The terms "residues" and "structural units", used in reference to the constituents of the polymers, are synonymous throughout the specification.

The term "carbonate group" as used herein is represented by the formula OC(O)OR, where R can be hydrogen, an alkyl, alkenyl, alkynyl, cycloalkyl, halogenated alkyl, or heterocycloalkyl group described above.

As used herein, the terms "number-average molecular weight" or "$M_n$" can be used interchangeably, and refer to the statistical average molecular weight of all the polymer chains in the sample and is defined by the formula:

$$M_n = \frac{\sum N_i M_i}{\sum N_i}$$

where $M_i$ is the molecular weight of a chain and $N_i$ is the number of chains of that molecular weight. $M_n$ can be determined for polymers, e.g., polycarbonate polymers, by methods well known to a person having ordinary skill in the art using molecular weight standards, e.g., polycarbonate standards, polystyrene standards or poly(methyl methacrylate) standards, preferably certified or traceable molecular weight standards.

As used herein, the terms "weight average molecular weight" or "$M_w$" can be used interchangeably, and are defined by the formula:

$$M_w = \frac{\sum N_i M_i^2}{\sum N_i M_i}$$

where $M_i$ is the molecular weight of a chain and $N_i$ if the number of chains of that molecular weight. Compared to $M_n$, $M_w$ takes into account the molecular weight of a given chain in determining contributions to the molecular weight average. Thus, the greater the molecular weight of a given chain, the more the chain contributes to the $M_w$. $M_w$ can be determined for polymers, e.g., polycarbonate polymers, by methods well known to a person having ordinary skill in the art using molecular weight standards, e.g., polycarbonate standards, polystyrene standards or poly(methyl methacrylate) standards, preferably certified or traceable molecular weight standards.

As used herein, the terms "polydispersity index" or "PDI" can be used interchangeably, and are defined by the formula:

$$PDI = \frac{M_w}{M_n}$$

the PDI has a value equal to or greater than 1, but as the polymer chains approach uniform chain length, the PDI approaches unity.

The terms "residues" and "structural units", used in reference to the constituents of the polymers, are synonymous throughout the specification.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

Each of the materials disclosed herein are either commercially available and/or the methods for the production thereof are known to those of skill in the art.

All documents cited in the present specification are hereby incorporated by reference in their entirety.

B. ACIDIC CATALYST

The present process for making ortho alkoxy bisphenol monomers, comprises the step of contacting at least one (alk-1-enyl)alkoxyphenol; comprises the step of contacting at least one alkoxyphenol; with at least one acidic catalyst as defined herein.

The term "acidic catalyst" as used herein refers to a soluble acid, an acidic ion-exchange resin, an acidic clay, or an acidic zeolite. Preferably, the acidic catalyst is an anhydrous strongly Brønsted acidic catalyst.

The term "soluble acid" as used herein refers to both inorganic acids (i.e., mineral acids) and organic acids. The inorganic acids comprises both hydrohalic acids (i.e., hydracids) and oxyacids.

Non-limiting examples of hydrohalic acids include hydrogen chloride (HCl), hydrogen bromide (HBr) and hydrogen iodide (HI). Non-limiting examples of oxyacids include sulfuric acid ($H_2SO_4$), (ortho)phosphoric acid ($H_3PO_4$), polyphosphoric acids (i.e., $H_4P_2O_7$, $H_5P_3O_{10}$, $H_6P_4O_{13}$ and $H_3P_3O_9$). The organic acids comprises both sulfonic acids and fluorinated sulfonic acids, which can be either aliphatic or aromatic. Non-limiting examples of sulfonic acids include methanesulfonic acid, trifluoromethanesulfonic acid and p-toluenesulfonic acid.

The term "ion-exchange resin" or "ion-exchange polymer" as used herein refers to a resin or polymer that acts as a medium for ion exchange, synthesized from an organic polymer substrate. The organic polymer substrate is a sulfonated polystyrene divinylbenzene or a sulfonated tetrafluoroethylene-based fluoropolymer-copolymer, resulting in a strongly acidic cation exchange resin or polymer. Non-limiting examples include Amberlyst-15, Amberlyst-XN1010, Dowex DR2030, Nafion NR50 and Nafion SAC13.

The term "acidic clay" as used herein refers to acid-activated montmorillonite, bentonite and kaolinite clays, which can be swelling or non-swelling clay materials. Non-limiting examples include montmorillonite K10, K30 or KSF The term "zeolite" as used herein refers to both natural and synthetic microporous crystalline aluminosilicate materials having a definite crystalline structure as determined by X-ray diffraction.

A zeolite comprises a system of channels which may be interconnected with other channel systems or cavities such as side-pockets or cages. The channel systems may be three-dimensional, two-dimensional or one-dimensional. A zeolite comprises $SiO_4$ and $XO_4$ tetrahedra, wherein X is Al (aluminium) or B (boron). A zeolite may comprise a combination of $AlO_4$ and $BO_4$ tetrahedra. In a preferred embodiment, X is Al, and the zeolite comprises no $BO_4$ tetrahedra. The $SiO_4$ and $XO_4$ tetrahedra are linked at their corners via a common oxygen atom. The Atlas of Zeolite Framework Types (C Baerlocher, L B McCusker, D H Olson, 6$^{th}$ ed. Elsevier, Amsterdam, 2007) in conjunction with the web-based version (http://www.iza-structure.org/databases/") is a compendium of topological and structural details about zeolite frameworks, including the types of ring structures present in the zeolite and the dimensions of the channels defined by each ring type. Proven recipes and good laboratory practice for the synthesis of zeolites can be found in the "Verified synthesis of zeolitic materials" 2$^{nd}$ Edition 2001. Various proven recipes for the synthesis comprising $BO_4$ tetrahedra are available. For example, the synthesis and characterization of boron-based zeolites having a MFI topology has been described by Cichocki and Parasiewicz-Kaczmarska (Zeolites 1990, 10, 577-582).

Suitable zeolites for use in the present process typically comprise:

at least two, preferably two or three, interconnected and non-parallel channel systems wherein at least one of said channel systems comprises 10- or more-membered ring channels; and a framework $Si/X_2$ ratio of at least 24 as measured by NMR; or three interconnected and non-parallel channel systems wherein at least two of said channel systems comprise 10- or more-membered ring channels, and a framework $Si/X_2$ ratio of at least 12 as measured by NMR;

wherein each X is Al or B.

As used herein, the term "channel system" refers to a system of parallel and crystallographically equivalent channels, wherein the channels are 8-membered ring channels or larger, for example wherein the channels are 10-membered ring channels or 12-membered ring channels. Accordingly, as used herein, the term "channel" refers to an 8- or more membered ring channel which is part of a system of parallel and crystallographically equivalent channels.

Suitable zeolites for use in the present process comprise 10- or more-membered ring channels, such as 10-membered ring channels (10MR), 12-membered ring channels (12MR), or larger. The ring size for each known zeolite framework type is provided in the Atlas of Zeolite Framework Types (C Baerlocher, LB McCusker, DH Olson, 6$^{th}$ ed. Elsevier, Amsterdam, 2007), which is incorporated herein by reference.

As used herein the terms "8-membered ring channels" or "8MR" refer to a channel comprising unobstructed 8-membered rings, wherein the 8-membered rings define the smallest diameter of the channel. An 8-membered ring comprises 8 T atoms, and 8 alternating oxygen atoms (forming the ring), wherein each T is Si, Al or B. As used herein the terms "10-membered ring channels" or "10MR" refers to a channel comprising unobstructed 10-membered rings, wherein the 10-membered rings define the smallest diameter of the channel. A 10-membered ring comprises 10 T atoms, and 10 alternating oxygen atoms (forming the ring), wherein each T is Si, Al or B. As used herein the terms "12-membered ring channels" or "12MR" refers to a channel comprising unobstructed 12-membered rings, wherein the 12-membered rings define the smallest diameter of the channel. A 12-membered ring comprises 12 T atoms, and 12 alternating oxygen atoms (forming the ring), wherein each T is Si, Al or B. As used herein, the term "10-or-more-membered ring channel" refers to a 10-membered ring channel or larger, and therefore comprises for example both 10-membered ring channels and 12-membered ring channels.

The framework $Si/X_2$ ratio may be determined via Nuclear Magnetic Resonance (NMR) measurements, more particularly $^{29}Si$ and $^{27}Al$ NMR. In a preferred embodiment, there is no framework B, and the $Si/X_2$ ratio is equal to the $Si/Al_2$ ratio. The determination of the $Si/Al_2$ ratio by NMR may be performed as described by Klinowski (Ann. Rev. Mater. Sci. 1988, 18, 189-218); or as described by G. Engelhardt and D. Michel (High-Resolution Solid-State NMR of Silicates and Zeolites. John Wiley & Sons, Chichester 1987. xiv, 485 pp). The determination of the Si/B2 ratio by NMR may be performed as discussed by D. Trong On et al. (Studies in Surface Science and Catalysis 1995, 97, 535-541; Journal of Catalysis, November 1995, Volume 157, Issue 1, Pages 235-243).

The present inventors have found that, by using certain zeolites as catalysts, ortho alkoxy bisphenol monomers can be simply synthesized. The present inventors have found that the use of zeolites as defined herein allow for the production of ortho alkoxy bisphenol monomers from a renewable aromatic feedstock, without the need for (in) soluble sulfur-containing cocatalysts to steer the regioselectivity. Additionally, in contrast with the classic hydroxyalkylation process, no water and aldol byproducts are formed, thus avoiding the extensive purification. Zeolites are heterogeneous catalysts, and are therefore easy to separate from the product after reaction, in contrast with classic homogeneous catalysts such as sulfuric acid. Zeolites are thermostable catalysts and can therefore be regenerated by calcination, in contrast with classic thermolabile ion-exchange resins such as Amberlyst-15. Furthermore, these ortho alkoxy bisphenol monomers are significantly less able to displace the natural estradiol from estrogen receptors. Without wishing to be bound by theory, this is believed to be related to the ortho alkoxy group(s) next to the phenolic hydroxyl group.

The present process comprises the step of contacting at least one (alk-1-enyl)alkoxyphenol; the step of contacting at least one alkoxyphenol; with at least one acidic catalyst; wherein said acidic catalyst comprises a soluble acid, an acidic ion-exchange resin, an acidic clay or an acidic zeolite, wherein said zeolite comprises:

at least two, preferably two or three, interconnected and non-parallel channel systems, wherein at least one of the channel systems comprises 10- or more-membered ring channels; and a framework $Si/X_2$ ratio of at least 24 as measured by NMR; or three interconnected and non-parallel channel systems wherein at least two of the channel systems comprise 10- or more-membered ring channels, and a framework $Si/X_2$ ratio of at least 12 as measured by NMR, wherein each X is Al or B.

and wherein said (alk-1-enyl)alkoxyphenol is an 3-(alk-1-enyl)alkoxyphenol, an 4-(alk-1-enyl)alkoxyphenol, an 5-(alk-1-enyl)alkoxyphenol or an 6-(alk-1-enyl)alkoxyphenol, and wherein said alkoxyphenol is a 2-alkoxyphenol, a 3-alkoxyphenol, a 2,3-dialkoxyphenol, or a 2,6-dialkoxyphenol, preferably wherein "channel system" refers to a system of parallel and crystallographically equivalent channels, wherein the channels are 8-membered ring channels or larger.

Indeed, the inventors have found that the regioselectivity towards p,p'- and m,p'-substituted ortho alkoxy bisphenol monomers highly depends on the zeolite architecture. It was found that the best results were obtained using zeolites comprising at least two interconnected and non-parallel channel systems (a 2D or 3D micropore geometry). Accordingly, the zeolites used in the process described herein comprise a 2D or 3D micropore geometry, more particularly an interconnected 2D or 3D micropore geometry.

Furthermore, zeolites suitable for the process described herein have channels which are large enough to accommodate the catalysis of the reaction from (alk-1-enyl)alkoxyphenol and alkoxyphenol molecules to the respective ortho alkoxy bisphenol monomer. The inventors found that the best results were obtained with zeolites comprising at least one 10- or more-membered ring channel.

The present inventors have further found that the $Si/X_2$ ratio in the zeolite framework significantly influences the suitability of the zeolites for catalyzing the reaction of (alk-1-enyl)alkoxyphenol and alkoxyphenol to ortho alkoxy bisphenol monomers.

Accordingly, in particular embodiments, the zeolite(s) for use in the process described herein may comprise a framework $Si/X_2$ ratio of at least 24, for example a framework $Si/Al_2$ ratio of at least 24, wherein the zeolite further comprises at least two interconnected and non-parallel channel systems wherein at least one of the interconnected and non-parallel channel systems comprises 10- or more-membered ring channels, i.e., at least one of the channel systems comprises 10- or more-membered ring channels, and at least one other channel system comprises 8- or more-membered ring channels. Examples of such zeolites are zeolites comprising a topology selected from the group comprising FER, MFI, and MWW.

In yet further embodiments, both of the at least two channel systems comprise 10- or more-membered ring channels. In particular embodiments, at least one of the channel systems comprises 12- or more-membered ring channels.

In certain embodiments, the zeolite for use in the process described herein may comprise a framework $Si/X_2$ ratio of at least 12, for example a framework $Si/Al_2$ ratio of at least 12; wherein the zeolite further comprises three interconnected and non-parallel channel systems wherein at least two of the interconnected and non-parallel channel systems comprise 10- or more-membered ring channels, i.e., at least two of the channel systems comprise 10- or more-membered ring channels, and the other channel system comprises 8- or more-membered ring channels. Examples of such zeolites include, but are not limited to zeolites comprising a topology selected from the group comprising BEA, FAU, and MEL.

In yet further embodiments, the three channel systems all comprise 10- or more-membered ring channels. In particular embodiments, at least one of the channel systems comprises 12- or more-membered channels. In certain embodiments, at least two of the channel systems comprise 12- or more-membered ring channels. Examples of such zeolites include, but are not limited to zeolites comprising a topology selected from the group comprising BEA and FAU.

In particular embodiments, the zeolite comprises at least two interconnected and non-parallel channel systems wherein at least one of the interconnected and non-parallel channel systems comprises 10- or more-membered ring channels; wherein the zeolite further comprises a framework $Si/X_2$ ratio of at least 24, more particularly of at least 25, for example a ratio of at least 30, for example a ratio of at least 35, for example a ratio of at least 40, for example a ratio of at least 50, for example a ratio of at least 60, for example a ratio of at least 70, for example a ratio of at least 80, for example a ratio of at least 90, for example or at least 100. Preferably, the zeolite comprises two or three interconnected and non-parallel channel systems wherein at least one of the interconnected and non-parallel channel systems comprises 10- or more-membered ring channels; wherein the zeolite further comprises a framework $Si/Al_2$ ratio of at least 24, more particularly a ratio of at least 25, for example a ratio of at least 30, for example a ratio of at least 35, for example a ratio of at least 40, for example a ratio of at least 50, for example a ratio of at least 60, for example a ratio of at least 70, for example a ratio of at least 80, for example a ratio of at least 90, or for example a ratio of at least 100.

In particular embodiments, the zeolite comprises three interconnected and non-parallel channel systems wherein at least two of the interconnected and non-parallel channel systems comprise 10- or more-membered ring channels; wherein the zeolite further comprises a framework $Si/X_2$ ratio of at least 6, more particularly at least 8, for example a ratio of at least 10, for example a ratio of at least 15, for example a ratio of at least 20, for example a ratio of at least 25, for example a ratio of at least 30, for example a ratio of at least 35, for example a ratio of at least 40, for example a ratio of at least 50, for example a ratio of at least 60, for example a ratio of at least 70, for example a ratio of at least 80, for example a ratio of at least 90, or for example a ratio of at least 100. Preferably, the zeolite comprises three interconnected and non-parallel channel systems wherein at least two of the interconnected and non-parallel channel systems comprise 10- or more-membered ring channels; wherein the zeolite further comprises a framework $Si/Al_2$ ratio of at least 12, more particularly of at least 15, for example a ratio of at least 20, for example a ratio of at least 25, for example a ratio of at least 30, for example a ratio of at least 35, for example a ratio of at least 40, for example a ratio of at least 50, for example a ratio of at least 60, for example a ratio of at least 70, for example a ratio of at least 80, for example a ratio of at least 90, or for example a ratio of at least 100.

In most embodiments, the conversion of (alk-1-enyl)alkoxyphenol and alkoxyphenol to ortho alkoxy bisphenol monomer increases as the $Si/X_2$ ratio increases, preferably as the $Si/Al_2$ ratio increases. In some embodiments, it is observed that at high $Si/X_2$ ratios, the conversion may decrease as the $Si/X_2$ ratio increases further. Without wishing to be bound by theory, this is believed to be related to the low amount of acid sites in zeolites with high $Si/X_2$ ratio. Therefore, in particular embodiments, the zeolite has a framework $Si/X_2$ ratio below 280. In further embodiments, the zeolite has a framework $Si/X_2$ ratio below 200. Preferably, the zeolite has a framework $Si/Al_2$ ratio below 280. In further embodiments, the zeolite has a framework $Si/Al_2$ ratio below 200.

The zeolites used in the process described herein may comprise $AlO_4$ tetrahedra, $BO_4$ tetrahedra, or both. Accordingly, in some embodiments, $X_2$ is $(Al_2+B_2)$. Thus, for a given zeolite, the $Si/X_2$ framework ratio remains the same upon substitution of framework Al by B, or vice versa. However, it is envisaged that in particular embodiments, the zeolites may not comprise $BO_4$ tetrahedra, or an insignificant amount thereof (e.g., an Al/B ratio of 100 or more). Thus, in particular embodiments, $X_2$ may be $Al_2$.

The $Si/X_2$ ratios referred to herein are molar ratios as determined via NMR, unless specified otherwise. It will be understood by the skilled person that the $Si/X_2$ ratio referred to herein is equal to the $SiO_2/X_2O_3$ molar ratio, wherein $X_2O_3$ is ($Al_2O_3$ and/or $B_2O_3$). Moreover, the skilled person will understand that by dividing the $Si/X_2$ ratio by two, the Si/X molar ratio is obtained, wherein X is (Al and/or B).

Preferably, the channels defined by the zeolite topology are large enough to be accessible for the (alk-1-enyl)alkoxyphenol and alkoxyphenol, but small enough to prevent significant formation and/or diffusion of trimers or higher order oligomers. Accordingly, in particular embodiments, the zeolite only comprises channels with a ring size of at most 18, preferably of at most 14, for example of at most 12.

In a preferred embodiment, suitable zeolites for use in the process described herein comprises a topology selected from the group comprising BEA, MFI, FAU, MEL, FER, and MWW. The inventors have found that these zeolites provide a particularly high regioselectivity towards p,p'- and m,p'-substituted ortho alkoxy bisphenol monomers. In certain embodiments, the zeolite(s) comprise a topology selected from the group consisting of BEA, MFI, FAU, and MWW. In specific embodiments, the zeolite(s) comprise a zeolite with a FAU topology.

Exemplary commercially available zeolites suitable for use in the processes described herein include, but are not limited to, Beta polymorph A (BEA topology), ZSM-5 (Mobil; MFI topology), Y zeolite (FAU topology), and MCM-22 (Mobil; MWW topology).

In certain embodiments, the zeolite comprises channels having an average (equivalent) diameter of at least 4.5 Å. More particularly, the zeolite may comprise two or more non-parallel channels having an average diameter of at least 4.5 Å. The channel diameter may be determined theoretically via knowledge of the zeolite framework type, or via X-ray diffraction (XRD) measurements, as will be known by the skilled person. Preferably, the zeolite comprises two or more non-parallel and interconnected channels having an average (equivalent) diameter between 4.5 and 13.0 Å, more preferably between 4.5 and 8.5 Å. Preferably, the diameter for the appropriate topology is obtained from international standard literature: the Atlas of Zeolite structures or the corresponding online database, found at http://www.iza-structure.org/databases/, as referenced above. The (equivalent) diameter of the channels may also be determined experimentally via $N_2$ adsorption, for example as discussed by Groen et al. (*Microporous and Mesoporous Materials* 2003, 60, 1-17), Storck et al. (*Applied Catalysis A: General* 1998, 174, 137-146) and Rouquerol et al. (Rouquerol F, Rouquerol J and Sing K, *Adsorption by powders and porous solids: principles, methodology and applications*, Academic Press, London, 1999).

In some embodiments, the zeolite may further comprise mesopores. The presence of mesopores may increase the accessibility of both the (alk-1-enyl)alkoxyphenol and the alkoxyphenol to the micropores, and may therefore further increase the reaction speed. However, it is also envisaged that the zeolite may not comprise mesopores.

As used herein the term "mesopores" refers to pores in the zeolite crystal having average diameters of 2.0 nm to 50 nm. For pore shapes deviating from the cylinder, the above ranges of diameter of mesopores refer to equivalent cylindrical pores. The mesopore average diameter may be determined by gas sorption techniques such as $N_2$ adsorption.

The zeolite(s) may be used as such, for example as a powder. In certain embodiments, the zeolite(s) may be formulated into a catalyst by combining with other materials that provide additional hardness or catalytic activity to the finished catalyst product. Materials which can be blended with the zeolite may be various inert or catalytically active materials, or various binder materials. These materials include compositions such as kaolin and other clays, phosphates, alumina or alumina sol, titania, metal oxide such as zirconia, quartz, silica or silica sol, metal silicates, and mixtures thereof. These components are effective in densifying the catalyst and increasing the strength of the formulated catalyst. Various forms of rare earth metals can also be added to the catalyst formulation. The catalyst may be formulated into pellets, spheres, extruded into other shapes, or formed into spray-dried particles. The amount of zeolite which is contained in the final catalyst product may range from 0.5 to 99.9 weight %, preferably from 2.5 to 99.5 weight % of the total catalyst, preferably from 2.5 to 95 weight %, preferably from 2.5 to 90 weight % of the total catalyst, most preferably from 2.5 to 80 weight %; for example from 20 to 95 weight %, preferably from 20 to 90 weight %, most preferably from 20 to 80 weight %, with weight % based on the total weight of catalyst product.

In some embodiments, the zeolite(s) for use in the processes described herein can be exposed to a (post-synthesis) treatment to increase the $Si/X_2$ framework ratio. Methods to increase the $Si/Al_2$ ratio of zeolites are known in the art, and include dealumination of the framework via (hydro)thermal treatment, extraction of framework aluminum with acid, and replacement of framework aluminum with silicon by reaction with silicon halides or hexafluorosilicates. An exemplary method of dealumination is described by Remy et al. (*J. Phys. Chem.* 1996, 100, 12440-12447; hereby incorporated by reference).

The zeolites for use in the process described herein preferably are Brønsted acidic zeolites, i.e., having proton donating sites in the micropores. In some embodiments, the zeolite has a Brønsted acid density between 0.05 and 6.5 mmol/g dry weight. When all Al T-sites are counterbalanced with an acidic proton (as opposed to a cation), the Brønsted acid density can be directly derived from the $Si/Al_2$ ratio, for example as discussed in *The Handbook of Heterogeneous Catalysis*, $2^{nd}$, edited by G. Ertl, H. Knozinger, F. Schtith and J. Weitkamp, Wiley 2008.

The zeolites for use in the processes described herein can be obtained in acidic form (acidic H-form zeolite) or (partly) exchanged with a cation other than $H^+$. In some embodiments, the acidic H-form zeolites can be used as such. In some other embodiments, the zeolites for use in the processes described herein can be exposed to a (post-synthesis) treatment to increase the Brønsted acid density. Brønsted acid sites in zeolites can be readily generated by aqueous ion exchange with an ammonium salt, followed by thermal decomposition of the ammonium ions inside the zeolite.

Alternatively, the acid sites may be generated by aqueous ion exchange with the salt of a multivalent metal cation (such as $Mg2+$, $Ca2+$, $La3+$, or mixed rare-earth cations), followed by thermal dehydration (J. Weitkamp, *Solid State Ionics* 2000, 131, 175-188; hereby incorporated by reference).

In contrast with polymeric catalysts (e.g., Amberlyst™), the zeolite catalysts described herein may be regenerated and reused in the process. Accordingly, particular embodiments of the process described herein may comprise a step of regenerating the zeolite catalyst. Regeneration of the zeolite catalysts can be performed via washing or calcination. Preferably, regeneration of the zeolite catalysts is done via calcination, for example at a temperature of at least 150° C. In particular embodiments, the calcination temperature is at least 200° C., for example at least 300° C., for example at least 400° C., for example about 450° C.

C. (ALK-α-ENYL)ALKOXYPHENOL AND ALKOXYPHENOL

In the processes described herein, at least one (alk-1-enyl) alkoxyphenol and at least one alkoxyphenol is used as starting material.

The (alk-1-enyl)alkoxyphenol used in the context of the processes described herein is selected from an 3-(alk-1-enyl) alkoxyphenol, an 4-(alk-1-enyl)alkoxyphenol, an 5-(alk-1- enyl)alkoxyphenol or an 6-(alk-1-enyl)alkoxyphenol. For functionalized alk-1-enyl groups, e.g., hydroxyalk-1-enyl or carboxyalk-1-enyl groups, also ethers, esters, amides, imides or salts of such compounds may be used. The alkoxyphenol used in the context of the processes described herein is selected from a 2-alkoxyphenol, a 3-alkoxyphenol, a 2,3-dialkoxyphenol, or a 2,6-dialkoxyphenol.

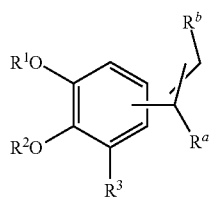

(I)

In some embodiments, the acidic catalyst is contacted with at least one compound of formula (I)
wherein if $R^1$ is hydrogen than $R^2$ is independently a group selected from $C_{1-6}$alkyl; $C_{6-10}$aryl; $C_{1-10}$alkyl$C_{6-10}$aryl; or $C_{6-10}$aryl$C_{1-6}$alkyl; each group being optionally substituted by one or more substituents selected from $C_{1-6}$alkyl, $C_{1-6}$alkoxy; and $R^3$ is independently hydrogen, hydroxyl or a group selected from $C_{1-6}$alkyl; $C_{1-6}$alkoxy; $C_{6-10}$aryl; $C_{1-6}$alkyl$C_{6-10}$aryl; or $C_{6-10}$aryl$C_{1-6}$alkyl; each group being optionally substituted by one or more substituents selected from $C_{1-6}$alkyl, $C_{1-6}$alkoxy; and
wherein if $R^2$ is hydrogen than $R^1$ is independently a group selected from $C_{1-6}$alkyl; $C_{6-10}$aryl; $C_{1-6}$alkyl$C_{6-10}$aryl; or $C_{6-10}$aryl$C_{1-6}$alkyl; each group being optionally substituted by one or more substituents selected from $C_{1-6}$alkyl, $C_{1-6}$alkoxy; and $R^3$ is independently hydroxyl or a group selected $C_{1-6}$alkyl; $C_{1-6}$alkoxy; $C_{6-10}$aryl; $C_{1-6}$alkyl$C_{6-10}$aryl; or $C_{6-10}$aryl$C_{1-6}$alkyl; each group being optionally substituted by one or more substituents selected from $C_{1-6}$alkyl, $C_{1-6}$alkoxy; and
wherein $R^a$ is independently hydrogen or a group selected from $C_{1-6}$alkyl; $C_{6-10}$aryl; $C_{1-6}$alkyl$C_{6-10}$aryl; or $C_{6-10}$aryl$C_{1-6}$alkyl; each group being optionally substituted by one or more substituents selected from $C_{1-6}$alkyl, $C_{1-6}$alkyloxy; and $R^b$ is independently hydrogen or a group selected from $C_{1-6}$alkyl; $C_{6-10}$aryl; hydroxy$C_{1-6}$alkyl; $C_{1-6}$alkoxy$C_{1-6}$alkyl; $C_{1-6}$carboxy$C_{1-6}$alkyl; $C_{1-6}$alkyl$C_{6-10}$aryl; or $C_{6-10}$aryl$C_{1-6}$alkyl; or an ether, an ester, an amide, an imide or a salt thereof; each group being optionally substituted by one or more substituents selected from $C_{1-6}$alkyl, $C_{1-6}$alkoxy; and at least one compound of formula (II)

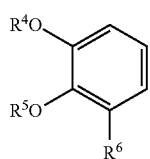

(II)

wherein if $R^4$ is hydrogen than $R^5$ is independently a group selected from $C_{1-6}$alkyl; $C_{6-10}$aryl; $C_{1-6}$alkyl$C_{6-10}$aryl; or $C_{6-10}$aryl$C_{1-6}$alkyl; each group being optionally substituted by one or more substituents selected from $C_{1-6}$alkyl, $C_{1-6}$alkoxy; and $R^6$ is independently hydrogen, hydroxyl or a group selected from $C_{1-6}$alkyl; $C_{1-6}$alkoxy; $C_{6-10}$aryl; $C_{1-6}$alkyl$C_{6-10}$aryl; or $C_{6-10}$aryl$C_{1-6}$alkyl; each group being optionally substituted by one or more substituents selected from $C_{1-6}$alkyl, $C_{1-6}$alkoxy; and
wherein if $R^5$ is hydrogen than $R^4$ is independently a group selected from $C_{1-6}$alkyl; $C_{6-10}$aryl; $C_{1-6}$alkyl$C_{6-10}$aryl; or $C_{6-10}$aryl$C_{1-6}$alkyl; each group being optionally substituted by one or more substituents selected from $C_{1-6}$alkyl, $C_{1-6}$alkoxy; and $R^6$ is independently hydroxyl or a group selected $C_{1-6}$alkyl; $C_{1-6}$alkoxy; $C_{6-10}$aryl; $C_{1-10}$alkyl$C_{6-10}$aryl; or $C_{6-10}$aryl$C_{1-6}$alkyl; each group being optionally substituted by one or more substituents selected from $C_{1-6}$alkyl, $C_{1-6}$alkoxy;

In particular embodiments, at least one of $R^a$ and $R^b$ is not hydrogen. Unless expressly stated otherwise, each of the following terms has the indicated meaning:

The term "$C_{1-6}$alkyl", as a group or part of a group, refers to a hydrocarbyl radical of Formula $C_nH_{2n+1}$ wherein n is a number ranging from 1 to 6. Generally, the alkyl groups comprise from 1 to 6 carbon atoms, for example 1 to 4 carbon atoms. Alkyl groups may be linear, or branched and may be substituted as indicated herein. When a subscript is used herein following a carbon atom, the subscript refers to the number of carbon atoms that the named group may contain. Thus, for example, $C_{1-4}$alkyl means an alkyl of 1 to 4 carbon atoms. Examples of alkyl groups are methyl, ethyl, propyl, isopropyl, butyl, isobutyl, sec-butyl, tert-butyl, pentyl and its chain isomers, hexyl and its chain isomers.

As used herein, the term "$C_{6-10}$aryl", by itself or as part of another substituent, refers to a polyunsaturated, aromatic hydrocarbyl group having a single ring (i.e., phenyl) or multiple aromatic rings fused together (e.g., naphthalene), or linked covalently, typically containing 6 to 10 atoms; wherein at least one ring is aromatic. Examples of $C_{6-10}$aryl include phenyl, naphthyl, indanyl, or 1,2,3,4-tetrahydronaphthyl.

The term "$C_{1-6}$alkoxy" or "$C_{1-6}$alkyloxy" as used herein refers to a radical having the formula —$OR^d$ wherein $R^d$ is $C_{1-6}$alkyl; $C_{6-10}$aryl; $C_{6-10}$aryl$C_{1-6}$alkyl; or $C_{6-10}$aryl$C_{1-6}$alkyl. Non-limiting examples of suitable alkoxy include methoxy, ethoxy, propoxy, isopropoxy, butoxy, isobutoxy, sec-butoxy, tert-butoxy, pentyloxy and its chain isomers, hexyloxy and its chain isomers, phenoxy, guaiacoxy, syringoxy, naphthoxy and benzoxy.

The term "hydroxy$C_{1-6}$alkyl", as a group or as part of a group, means a $C_{1-6}$alkyl as defined herein, wherein a hydrogen atom is replaced by an hydroxyl group. A non-limiting example of an hydroxyalkyl group includes hydroxymethyl (—$CH_2$—OH).

As used herein, the term "$C_{1-6}$alkoxy$C_{1-6}$alkyl", by itself or as part of another substituent, refers to a $C_{1-6}$alkyl group as defined herein, wherein a hydrogen atom is replaced by a $C_{1-6}$alkoxy as defined herein. Non-limiting examples of an alkoxyalkyl group include methoxylmethyl (—$CH_2$—O—$CH_3$) and ethoxymethyl (—$CH_2$—O—$C_2H_5$).

As used herein, the term "carboxy$C_{1-6}$alkyl" as a group or as part of a group, means a $C_{1-6}$alkyl as defined herein, wherein a hydrogen atom is replaced by an carboxyl group. A non-limiting example of an carboxyalkyl group includes carboxymethyl (—$CH_2$—(CO)OH).

The term "$C_{6-10}$aryl$C_{1-6}$alkyl", as a group or part of a group, means a $C_{1-6}$alkyl as defined herein, wherein a hydrogen atom is replaced by a $C_{6-10}$aryl as defined herein. Non-limiting examples of $C_{6-10}$aryl$C_{1-6}$alkyl radicals include benzyl, phenethyl, dibenzylmethyl, methylphenylmethyl, 3-(2-naphthyl)-butyl, and the like.

As used herein, the term "$C_{1-6}$alkyl$C_{6-10}$aryl", by itself or as part of another substituent, refers to a $C_{6-10}$aryl group as defined herein, wherein a hydrogen atom is replaced by a $C_{1-6}$alkyl as defined herein.

In certain embodiments, the (alk-1-enyl)alkoxyphenol (also referred to as "(alk-α-enyl)alkoxyphenol or "(α-alkenyl)alkoxyphenol") is a compound of formula (I) wherein if $R^1$ is hydrogen than $R^2$ is independently a group selected from $C_{1-6}$alkyl; $C_{6-10}$aryl; $C_{1-10}$alkyl$C_{6-10}$aryl; or $C_{6-10}$aryl$C_{1-6}$alkyl; each group being optionally substituted by one or more substituents selected from $C_{1-6}$alkyl, $C_{1-6}$alkoxy; and $R^3$ is independently hydrogen, hydroxyl or a group selected from $C_{1-6}$alkyl; $C_{1-6}$alkoxy; $C_{6-10}$aryl; $C_{1-6}$alkyl$C_{6-10}$aryl; or $C_{6-10}$aryl$C_{1-6}$alkyl; each group being optionally substituted by one or more substituents selected from $C_{1-6}$alkyl, $C_{1-6}$alkoxy; preferably $R^2$ is independently $C_{1-6}$alkyl or $C_{6-10}$aryl; and preferably $R^3$ is independently hydrogen, hydroxyl or $C_{1-6}$alkoxy; preferably $R^2$ is independently methoxy or ethoxy; and preferably $R^3$ is independently hydrogen, hydroxyl, methoxy or ethoxy; and wherein if $R^2$ is hydrogen than $R^1$ is independently a group selected from $C_{1-6}$alkyl; $C_{6-10}$aryl; $C_{1-6}$alkyl$C_{6-10}$aryl; or $C_{6-10}$aryl$C_{1-6}$alkyl; each group being optionally substituted by one or more substituents selected from $C_{1-6}$alkyl, $C_{1-6}$alkoxy; and $R^3$ is independently hydroxyl or a group selected $C_{1-6}$alkyl; $C_{1-6}$alkoxy; $C_{6-10}$aryl; $C_{1-6}$alkyl$C_{6-10}$aryl; or $C_{6-10}$aryl$C_{1-6}$alkyl; each group being optionally substituted by one or more substituents selected from $C_{1-6}$alkyl, $C_{1-6}$alkoxy; preferably $R^1$ is independently $C_{1-6}$alkyl or $C_{6-10}$aryl; and preferably $R^3$ is independently hydroxyl or $C_{1-6}$alkoxy; preferably $R^1$ is methoxy or ethoxy; and $R^3$ is hydroxyl, methoxy or ethoxy. wherein $R^a$ is hydrogen and $R^b$ is a group selected from $C_{1-6}$alkyl; $C_{6-10}$aryl; hydroxy$C_{1-6}$alkyl; $C_{1-6}$alkoxy$C_{1-6}$alkyl; $C_{1-6}$carboxy$C_{1-6}$alkyl; $C_{1-6}$alkyl$C_{6-10}$aryl; or $C_{6-10}$aryl$C_{1-6}$alkyl; or an ether, an ester, an amide, an imide or a salt thereof; each group being optionally substituted by one or more substituents selected from $C_{1-6}$alkyl, $C_{1-6}$alkoxy; preferably $R^b$ is selected from $C_{1-6}$alkyl; hydroxy$C_{1-6}$alkyl; $C_{1-6}$alkoxy$C_{1-6}$alkyl; $C_{1-6}$carboxy$C_{1-6}$alkyl; preferably $R^b$ is hydrogen, methyl, hydroxymethyl, methoxymethyl, carboxymethyl or an ether, an ester, an amide, an imide or a salt thereof.

In preferred embodiments, the compound of formula (I) can be selected from the group comprising (alk-1-enyl)-2-alkoxyphenol, (alk-1-enyl)-3-alkoxyphenol, (alk-1-enyl)-2,3-dialkoxyphenol and (alk-1-enyl)-2,6-dialkoxyphenol. Preferably the compound of formula (I) is (alk-1-enyl)-2-alkoxyphenol or (alk-1-enyl)-2,6-dialkoxyphenol.

In preferred embodiments, the compound of formula (I) can be selected from the group comprising 3-(alk-1-enyl)-2-alkoxyphenol, 4-(alk-1-enyl)-2-alkoxyphenol, 5-(alk-1-enyl)-2-alkoxyphenol, or 6-(alk-1-enyl)-2-alkoxyphenol. Preferably the compound of formula (I) is 3-(alk-1-enyl)-2-alkoxyphenol, 4-(alk-1-enyl)-2-alkoxyphenol, or 5-(alk-1-enyl)-2-alkoxyphenol.

In preferred embodiments, the compound of formula (I) can be selected from the group comprising 4-(alk-1-enyl)-2-alkoxyresorcinol, or 5-(alk-1-enyl)-2-alkoxyresorcinol. Preferably the compound of formula (I) is 5-(alk-1-enyl)-2-alkoxyresorcinol.

In preferred embodiments, the compound of formula (I) can be selected from the group comprising 4-(alk-1-enyl)-3-alkoxycatechol, 5-(alk-1-enyl)-3-alkoxycatechol, or 6-(alk-1-enyl)-3-alkoxycatechol. Preferably the compound of formula (I) is 4-(alk-1-enyl)-3-alkoxycatechol, or 5-(alk-1-enyl)-3-alkoxycatechol.

In preferred embodiments, the compound of formula (I) can be selected from the group comprising 4-(alk-1-enyl)-2,3-dialkoxyphenol, 5-(alk-1-enyl)-2,3-dialkoxyphenol, or 6-(alk-1-enyl)-2,3-dialkoxyphenol. Preferably the compound of formula (I) 4-(alk-1-enyl)-2,3-dialkoxyphenol, or 5-(alk-1-enyl)-2,3-dialkoxyphenol.

In preferred embodiments, the compound of formula (I) can be selected from the group comprising 3-(alk-1-enyl)-2,6-dialkoxyphenol, or 4-(alk-1-enyl)-2,6-dialkoxyphenol. Preferably the compound of formula (I) 4-(alk-1-enyl)-2,6-dialkoxyphenol.

In preferred embodiments, the compound of formula (I) can be selected from the group comprising 4-vinylguaiacol, 4-vinylguaethol, 2-methoxy-5-vinylresorcinol, 3-methoxy-5-vinylcatechol, and 4-vinylsyringol. Preferably the compound of formula (I) is vinylguaiacol or vinylsyringol.

In preferred embodiments, the compound of formula (I) can be selected from the group comprising isoeugenol, propenylguaethol, 2-methoxy-5-(prop-1-en-yl)resorcinol, 3-methoxy-5-(prop-1-en-1-yl)catechol, and 4-(prop-1-en-1-yl)syringol. Preferably the compound of formula (I) is isoeugenol or 4-(prop-1-en-1-yl)syringol.

In preferred embodiments, the compound of formula (I) can be selected from the group comprising coniferyl alcohol, 5-(3-hydroxyprop-1-en-1-yl)-2-methoxyresorcinol, 5-hydroxyconiferyl alcohol, and sinapyl alcohol; and an ether or ester thereof. Preferably the compound of formula (I) is coniferyl alcohol or sinapyl alcohol; or an methyl ether or methyl ester thereof.

In preferred embodiments, the compound of formula (I) can be selected from the group comprising isoferulic acid, ferulic acid, 5-(2-carboxyeth-1-en-1-yl)-2-methoxyresorcinol, 5-hydroxyferulic acid, and sinapic acid; and an ester, an amide, an imide or salt thereof. Preferably the compound of formula (I) is ferulic acid or sinapic acid; or an methyl ester thereof.

In certain embodiments, the alkoxyphenol is a compound of formula (II) wherein if $R^4$ is hydrogen than $R^5$ is independently a group selected from $C_{1-6}$alkyl; $C_{6-10}$aryl; $C_{1-6}$alkyl$C_{6-10}$aryl; or $C_{6-10}$aryl$C_{1-6}$alkyl; each group being optionally substituted by one or more substituents selected from $C_{1-6}$alkyl, $C_{1-6}$alkoxy; and $R^6$ is independently hydrogen, hydroxyl or a group selected from $C_{1-6}$alkyl; $C_{1-6}$alkoxy; $C_{6-10}$aryl; $C_{1-6}$alkyl$C_{6-10}$aryl; or $C_{6-10}$aryl$C_{1-6}$alkyl; each group being optionally substituted by one or more substituents selected from $C_{1-6}$alkyl, $C_{1-6}$alkoxy; preferably $R^5$ is selected from $C_{1-6}$alkyl, or $C_{6-10}$aryl and $R^6$ is selected from hydrogen, hydroxyl, $C_{1-6}$alkoxy or $C_{6-10}$aryl; preferably $R^5$ is $C_{1-6}$alkyl and $R^6$ is hydrogen, hydroxyl or $C_{1-6}$alkoxy; and wherein if $R^5$ is hydrogen than $R^4$ is independently a group selected from $C_{1-6}$alkyl; $C_{6-10}$aryl; $C_{1-10}$alkyl$C_{6-10}$aryl; or $C_{6-10}$aryl$C_{1-6}$alkyl; each group being optionally substituted by one or more substituents selected from $C_{1-6}$alkyl, $C_{1-6}$alkoxy; and $R^6$ is independently hydroxyl or a group selected $C_{1-6}$alkyl; $C_{1-6}$alkoxy; $C_{6-10}$aryl; $C_{1-10}$alkyl$C_{6-10}$aryl; or $C_{6-10}$aryl$C_{1-6}$alkyl; each group being optionally substituted by one or more substituents selected from $C_{1-6}$alkyl, $C_{1-6}$alkoxy; preferably $R^4$ is selected from $C_{1-6}$alkyl, or $C_{6-10}$aryl and $R^6$ is selected from hydroxyl, $C_{1-6}$alkoxy or $C_{6-10}$aryl; preferably $R^4$ is $C_{1-6}$alkyl and $R_6$ is hydroxyl or $C_{1-6}$alkoxy;

In preferred embodiments, the compound of formula (II) can be selected from the group comprising 2-alkoxyphenol, 3-alkoxyphenol, 2,3-dialkoxyphenol and 2,6-dialkoxyphenol. Preferably the compound of formula (II) is 2-alkoxyphenol or 2,6-dialkoxyphenol.

In preferred embodiments, the compound of formula (II) can be selected from the group comprising guaiacol, guaethol and syringol. Preferably the compound of formula (II) is guaiacol or syringol.

D. ORTHO ALKOXY BISPHENOL MONOMER

The processes described herein may be used for the production of various ortho alkoxy bisphenol monomers, such as ortho di-alkoxy bisphenol monomers, ortho tri-alkoxy bisphenol monomers or ortho tetra-alkoxy bisphenol monomers.

In preferred embodiments, the ortho alkoxy bisphenol monomer prepared by the process described herein, is a compound of formula (III):

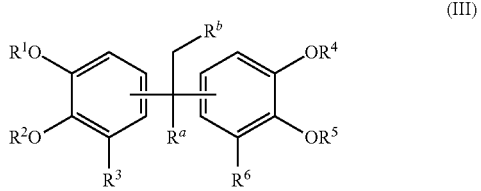

(III)

wherein $R^1$-$R^6$, $R^a$ and $R^b$ are as defined herein for formula (I) and formula (II); and wherein the bridging carbon group, connecting the two hydroxyl-substituted aryl groups, and the hydroxyl substituent (next to the alkoxy) on the aryl group are disposed ortho, meta or para to each other on the aryl group bearing the phenolic (—ArOH) functionality.

Compounds of formula (III) may be obtained by reaction of one or more compounds of both formula (I) and formula (II) as described herein.

In preferred embodiments, the ortho alkoxy bisphenol monomer prepared by the processes described herein is symmetric. In some embodiments, it is also envisaged that the ortho alkoxy bisphenol monomer may be asymmetric.

In certain embodiments, the bridging carbon group of the ortho alkoxy bisphenol monomer prepared by the processes described herein is either chiral or achiral. Preferably the bridging carbon group is achiral.

In some aspects, the disclosed ortho alkoxy bisphenol monomer is a bio-based material. In further aspects, the monomer is derived from a biological material. In some aspects, the monomer is wholly derived from a biological material. In other aspects, the monomer is partly derived from a biological material. In further aspects, the monomer is not derived from organic material that has been transformed by geological processes into petroleum, petrochemicals, and combinations thereof. In further aspects, the ortho alkoxy bisphenol monomer is from greater than 0 wt % to about 100 wt % derived from bio-based material, including exemplary wt % values of 1, 5, 10, 20, 30, 40, 50, 60, 70, 80, 90, and 99 wt. % derived from bio-based material. In still further aspects, the bio-based material comprises at least one lignocellulosic material, plant material, or a combination thereof. In even further aspects, bio-based material is a bio-based oil, pyrolysis oil, or lignin-rich waste from a biorefinery. In various aspects, a biological derived material, as described herein, can be determined by a carbon isotope ($^{13}C/^{14}C$) ratio, for example, as per ASTM D6866-12 "Standard Test Methods for Determining the Biobased Content of Solid, Liquid, and Gaseous Samples Using Radiocarbon Analysis".

E. USES OF ORTHO ALKOXY BISPHENOL MONOMERS

In certain embodiments the disclosed ortho alkoxy bisphenol monomers are valuable precursors for making renewable (bio)polymers, such as thermoplastics and/or thermoset resins.

In further embodiments the ortho alkoxy bisphenol monomers can be employed as additives, such as antioxidantia, UV-stabilizers and plasticizers.

In certain embodiments, the ortho alkoxy bisphenol monomers prepared by the processes described herein are converted to polymers. In particular embodiments said polymers are thermoplastics or thermosetting resins.

In certain embodiments, said polymers can be selected from the group comprising polycarbonates (PC), polyiminocarbonates (PIC), polyesters (PE), polyester-styrenes, polyurethanes, polyarylates, polyethers, polysulfones (PSU), polyarylsulfones, polyethersulfones (PESU), polyarylethersulfone (PAES), polyetheretherketones (PEEK), polyaryletherketones (PAEK), polyacetals, polyketones, alkylphenolic polymers, polyoxalates, polyalylates, epoxy resins, phenolic resins, vinyl ester resins, polyphenylene ether resins, polyphenylene sulphide resins, polyetherimide resins, cyanate ester resins, benzoxazine resins, bismaleimide resins and other end-capped resins and any combination thereof.

In certain embodiments, said polymers can be derived from one (i.e., homopolymers), or more than one species of monomer (i.e., copolymers), which can be linear or branched, and/or mixtures and/or combinations thereof. The class of copolymers comprises alternating copolymers, block copolymers, and graft copolymers. Other embodiments of the invention further include coatings or composites.

In preferred embodiments, said thermoplastics are polycarbonates, produced by reaction of at least one ortho alkoxy bisphenol monomer with a carbonate source selected from the group consisting of cyclic carbonates, dialkyl carbonates, diaryl carbonates, chloroformates, p-nitrophenyl chloroformate, phosgene, diphosgene, triphosgene (BTC), N,N'-carbonyldiimidazole (CDI), N,N'-disuccinimidyl carbonate (DSC), bis(2-pyridyl) carbonate, or N,N'-(carbonyldioxy) bisbenzotriazole.

In certain embodiments, said thermoplastics are polyesters, produced by reaction of at least one ortho alkoxy bisphenol monomer with a saturated or unsaturated aliphatic diacid, or derivatives thereof, which can be branched or unbranched, selected from the group consisting of $HO_2CXCO_2H$ with X selected from the group consisting of $C_{1-16}$alkyl, hydroxy$C_{1-16}$alkyl, $C_{1-6}$alkoxy$C_{1-16}$alkyl, carboxy$C_{1-16}$alkyl, $C_{6-10}$aryl$C_{1-6}$alkyl. Non-limiting examples include oxalic acid, malonic acid, maleic acid, fumaric acid, succinic acid, glutaric acid, adipic acid, pimelic acid, suberic acid, azelaic acid, sabacic acid, glutaconic acid, muconic acid, citraconic acid, mesaconic, itaconic acid, malic acid, aspartic acid, glutamic acid, tartronic acid, tartaric acid, diaminopimelic acid, saccharic acid, mesoxalic acid, oxaloacetic acid, and acetonedicarboxylic acid, and/or anhydrides, $C_{1-6}$alkyl esters, $C_{6-10}$aryl esters, acid chlorides and/or acid bromides thereof.

In preferred embodiments, said thermoplastics are polyesters, produced by reaction of at least one ortho alkoxy bisphenol monomer with an aromatic diacid selected from the group consisting of phthalic acid, isophthalic acid, terephthalic acid, diphenic acid, 2,6-naphthalenedicarboxylic acid, 2,3-furandicarboxylic acid, 2,4-furandicarboxylic acid, 2,5-furandicarboxylic acid, 3,4-furandicarboxylic acid, or corresponding thiophene or 1H-pyrrole analogues of aforementioned furan derivatives, and/or anhydrides, $C_{1-6}$alkyl esters, $C_{6-10}$aryl esters, acid chlorides and/or acid bromides thereof. Preferably the aromatic diacid is phthalic acid, isophthalic acid, terephthalic acid, and 2,5-furandicarboxylic acid, and corresponding thiophene or 1H-pyrrole analogues, and/or anhydrides, $C_{1-6}$alkyl esters, $C_{6-10}$aryl esters and/or acid chlorides thereof.

In further embodiments, said thermoplastics and thermosetting resins are produced by reaction of at least one ortho alkoxy bisphenol monomer with α,α'-dichloro-o-xylene, α,α'-dichloro-m-xylene, α,α'-dichloro-p-xylene, thionylchloride, sulfuryl chloride, bis(4-chlorophenyl) sulfone, other functionalized sulfones, dialkoxy methane, toluene diisocyanate, hexamethylene diisocyanate, methylene diphenyl diisocyanate, isophorone diisocyanate, (di)aldehydes (e.g., formaldehyde, 1,3,5-trioxane, acetaldehyde, paraldehyde, glyoxal, glyoxylic acid, malondialdehyde, succinaldehyde, glutaraldehyde, furfural), (di)ketones (e.g., acetone, methylglyoxal, 2,3-butanedione, 2,3-pentanedione), (di)amines (e.g., furfuryl amine, aniline, o-phenylenediamine, m-phenylenediamine, p-phenylenediamine, α,α'-diamino-o-xylene, α,α'-diamino-m-xylene, α,α'-diamino-p-xylene, bis(4-aminophenyl) sulfone, isophorone diamine), epichlorohydrin, oxalyl chloride, (meth)acrylic anhydride, (meth)acryloyl chloride, or cyanogen halides.

E. ASPECTS

In the process as described herein, the yield and selectivity towards ortho alkoxy bisphenol monomers may be dependent on the modus of operation (i.e., reactor configuration), which can be batch, semi-batch or continuous.

In certain embodiments the (alk-1-enyl)alkoxyphenol can selectively react towards the desired ortho alkoxy bisphenol monomers without formation of byproducts though competitive reaction pathways, enabling either a batch, semi-batch or continuous configuration. In particular embodiments the (alk-1-enyl)alkoxyphenol (A) can react through parallel, competitive reaction pathways yielding both desired ortho alkoxy bisphenol monomers (B) and undesired dimers (C), as expressed in the equations below:

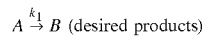
$A \xrightarrow{k_1} B$ (desired products)

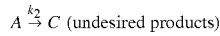
$A \xrightarrow{k_2} C$ (undesired products)

The corresponding rate expressions (for batch configuration) are:

$$\frac{dC_A}{dt} = -k_1 C_A^\alpha - k_2 C_A^\beta$$

$$\frac{dC_B}{dt} = +k_1 C_A^\alpha$$

$$\frac{dC_C}{dt} = +k_2 C_A^\beta$$

with $C_A$, $C_B$ and $C_C$ the concentration of compound A, B and C respectively, $k_1$ and $k_2$ the rate constants and α and β the reaction orders of respectively the desired and undesired reaction. If β>α, the concentration of reactant A, being the (alk-1-enyl)alkoxyphenol, should be kept at a low level in order to maximize selectivity, thereby favoring a semi-batch configuration. The case β>α occurs for an (alk-1-enyl)alkoxyphenol wherein $R^a$ is independently hydrogen or a group selected from $C_{1-6}$alkyl; and wherein $R^b$ is independently hydrogen or a group selected from $C_{1-6}$alkyl. Non-limiting examples of (alk-1-enyl)alkoxyphenol for which the reaction order β>α include (vinyl)-, (isoprop-1-enyl)- and (prop-1-enyl)alkoxyphenol such as vinylguaiacol, vinylsyringol, isoprop-1-enylguaiacol, isoprop-1-enylsyringol, isoeugenol and (prop-1-enyl)syringol.

In particular embodiments, the process as described herein, may be performed in semi-batch configuration wherein (alk-1-enyl)alkoxyphenol is added over time. The rate of addition is indicated by the normalized addition factor. As defined herein, the term "normalized addition factor" or "NAF" is expressed as the ratio of the total amount of added (alk-1-enyl)alkoxyphenol (in mole) divided by the total amount of initial alkoxyphenol, divided by the sum of the addition time and the total amount of Brønsted acidic catalytically active sites (in mole) present. For example when 1 mmol of (alk-1-enyl)alkoxyphenol is added to 20 mmol of alkoxyphenol over 2 hours in the presence of 0.1 mmol $H^+$, the normalized addition factor for this semi-batch configuration is 0.25. In particular embodiments, the process as described herein, may be performed in semi-batch configuration with a normalized addition factor ranging from about 0.5 to 0.001, from about 0.1 to 0.001, from about 0.02 to 0.001, an preferably from about 0.02 to 0.005.

In particular embodiments, the processes as described herein may be performed in batch configuration wherein all (alk-1-enyl)alkoxyphenol may be provided at the start of the reaction, in a composition, such as in a solvent or diluent, which comprises the (alk-1-enyl)alkoxyphenol, for example in concentrations of at least 1 weight % (wt %) based on the total weight of the composition, for example of at least 3 weight % (wt %) based on the total weight of the composition, for example of at least 5 weight % (wt %) based on the total weight of the composition, for example of at least 10 wt %, for example of at least 15 wt %, for example of at least 20 wt %, for example of at least 25 wt %, for example of at least 30 wt %, for example of at least 35 wt %, for example of at least 40 wt %, for example of at least 45 wt %, or for example of at least 50 wt % based on the total weight of the composition. In preferred embodiments, the (alk-1-enyl)alkoxyphenol may be provided in a composition comprising the 3-(alk-1-enyl)alkoxyphenol, 4-(alk-1-enyl)alkoxyphenol, 5-(alk-1-enyl)alkoxyphenol or 6-(alk-1-enyl)alkoxyphenol in a concentration of at least 1 weight % based on the total weight of the composition. In further embodiments, the composition may comprise the (alk-1-enyl)alkoxyphenol, preferably 4-(alk-1-enyl)alkoxyphenol or 5-(alk-1-enyl)alkoxyphenol, in a concentration of at least 5 wt %, for example of at least 5 wt %, for example of at least 10 wt %, for example of at least 15 wt %, for example of at least 20 wt %, for example of at least 25 wt %, for example of at least 30 wt %, for example of at least 35 wt %, for example of at least 40 wt %, for example of at least 45 wt %, or for example of at least 50 wt % based on the total weight of the composition.

In particular embodiments, the (alk-1-enyl)alkoxyphenol and the alkoxyphenol can be provided in solution or emulsion. In preferred embodiments, the (alk-1-enyl)alkoxyphenol is provided as a solution in (excess) alkoxyphenol (which acts as both reactant and solvent), without the use of unreactive external solvent(s), simplifying further downstream purification.

An appropriate external solvent may be one in which the (alk-1-enyl)alkoxyphenol, the alkoxyphenol and the ortho alkoxy bisphenol monomer described herein are soluble, which has an appropriate boiling point, which does not deactivate the acidic catalyst and which does not adversely affect the reaction in any way. More particularly, the boiling point preferably is sufficiently high so that the boiling point temperature exceeds the preferred temperature of reaction, but sufficiently low such that the energy required to distill the solvent is minimized. This may facilitate the separation of the ortho alkoxy bisphenol monomers from the reaction medium.

Solvents which are not preferred because of being potentially reactive with the (alk-1-enyl)alkoxyphenol, the alkoxyphenol and/or the ortho alkoxy bisphenol monomer and/or interfere with the catalytic process include water, alcohols, organic acids, esters and ethers containing alcohol, peroxide and/or acid impurities, ketones and aldehydes with a stable enol form, and amines.

Suitable solvents may include aliphatic hydrocarbon solvents such as n-pentane, isopentane, n-hexane, isohexane, n-heptane, isoheptane, 2,2,4-trimethylpentane, n-octane, isooctane, cyclohexane, methylcyclohexane, and cycloheptane; aromatic hydrocarbon solvent such as nitrobenzene; halogenated aliphatic hydrocarbon solvents such as chloroform and dichloromethane; nitrile solvents such as acetonitrile and propionitrile; ether solvents such as diethyl ether, isopropyl ether, n-butyl ether, n-hexylether, 2-ethylhexyl ether, ethylene oxide, 1,2-propylene oxide, dioxolane, 4-methyldioxolane, 1,4-dioxane, dimethyldioxane, ethylene glycol diethyl ether, ethylene glycol dibutyl ether, diethylene glycol diethyl ether, diethylene glycol di-n-butyl ether, tetrahydrofuran, and 2-methyltetrahydrofuran; and nitromethane.

In certain embodiments the processes as disclosed herein are performed under air. In various embodiments the processes as disclosed herein are performed under dry air containing no water vapor. In preferred embodiments the processes as disclosed herein are performed under inert atmosphere, devoid of oxygen and moisture, especially when both $R^a$ and $R^b$ are hydrogen (—H). The inert atmosphere comprises a gas selected from the group comprising nitrogen, argon or helium, and/or combinations thereof, which are inert gases at the temperature and pressures at which the process is performed.

The processes described herein may be performed at or near atmospheric pressure, and are typically performed at a pressure between 0.01 and 20 bar. In particular embodiments, the processes are performed at a pressure between 0.5 and 5 bar, more particularly between 0.9 and 1.1 bar.

The reaction may be performed at a relatively low temperature, and may therefore require less energy than other processes known in the art. In particular embodiments, the reaction is performed in liquid state at or near the melting temperature of the alkoxyphenol. In particular embodiments, the temperature of the reaction can be ranging from about 20 to 200° C. In preferred embodiments, the temperature of the reaction ranges from about 50-150° C., more particularly from about 80-120° C.

F. EXAMPLES

The following examples are put forth so as to provide those of ordinary skill in the art with a complete disclosure and description of how the compounds, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. Unless indicated otherwise, percentages referring to composition are in terms of wt %.

There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

General Methods and Materials

All materials and reagents were used as received from the supplier unless otherwise indicated. All chemicals were A.R. grade and other sources can be used besides the ones indicated below. Gas chromatography (GC) was performed using Agilent 6890 series auto-injector instrument equipped with a HP5-column and a flame-ionization detector (FID). $^1$H and $^{13}$C NMR analyses were performed using Bruker 300 and 400 MHz instruments to record Nuclear Magnetic Resonance (NMR) spectral measurements with a solution of monomer in deuterated chloroform (CDCl3).

Example 1—Preparation of GGP from Isoeugenol and Guaiacol

In this example several zeolites were tested as catalyst for the synthesis of GGP from 2-methoxy-4-(prop-1-enyl)phenol (isoeugenol) and 2-methoxyphenol (guaiacol).

The following zeolites were used: with FAU topology—CBV300, CBV500, CBV712, CBV720, CBV760, CBV780, HSZ-385HUA and HSZ-390HUA (available from Zeolyst International, in $NH_4$ or H-form); with BEA topology—CP814E*, CP814C* (available from Zeolyst International, in $NH_4$-form) and CZB150 (available from Sid-Chemie, in H-form) and HSZ-980HOA (available from Tosoh, in H-form); with MOR topology—CBV21A, CBV30A (available from Zeolyst International, in $NH_4$ or H-form) and HSZ-690HOA (available from Tosoh, in H-form); with MFI topology—CBV2314, CBV3024E, CBV5524G, CBV8014, CBV28014 (available from Zeolyst International, in $NH_4$-form); with TON topology—H-ZSM-22 (available from Bonding Chemical); with FER topology—HSZ-720NHA (available from Tosoh, in $NH_4$-form).

The zeolites were used in their Brønsted acidic form (H-form). In general, when zeolites were provided (partly) exchanged with other cations (such as Sodium cations), they were exchanged and calcined to maximize the acidity and achieve the H-form. Typically, 100 mL of an aqueous solution of 0.5 M $NH_4Cl$ was added per 1.0 gram of (e.g., Na) zeolite on wet basis. The mixture was heated for 4 hours under reflux conditions. Then, the zeolite was isolated by filtration and the exchange procedure was repeated. The zeolite was isolated again, and washed with 1 L of water. In this way, the $NH_4$-form of the zeolite is obtained. To transform this ammonium exchanged form into the Brønsted acidic form, the zeolite was typically calcined for 12 hours at a temperature of 550° C. A temperature ramp of 3° C./min was applied. The resulting zeolites were stored at room temperature in contact with air.

The zeolite was added to the reaction mixture, and the mixture was heated by placing the reaction flask in a hot oil bath at a temperature of about 80° C., and continuously mixed, the temperature of the reaction mixture being dependent on the used reagent and composition. Typically, the reaction was heated for about 2 hours under stirring, after which the mixture was cooled to room temperature. The relative amounts of isoeugenol, bisphenol and dimers in the reaction mixture after 2 hours was indicative of the yield obtainable with each catalyst, as the reaction mixture typically does not change significantly after 2 hours for a good catalyst. This can be appreciated from FIG. 11, which shows the relative amount of reaction products in a reactor at different times, using a H-CBV780 zeolite catalyst with a $Si/Al_2$ ratio of 80. However, it is noted that for some catalyst, the maximal concentrations may be obtained faster.

Reference experiments were conducted using the known catalysts sulfuric acid (about xx), p-toluenesulfonic acid monohydrate (pTSA.$H_2O$; about xx), Amberlyst® 15 Dry (about x.xg per xx mL solution). The amount of reference catalysts is chosen such that the total amount of acid sites is similar to the amount of acid sites of the zeolites, thus allowing a fair comparison.

For each experiment, the total conversion rate of isoeugenol, and GGP and dimer yields were determined using gas chromatography with flame ionization detector (GC/FID) (i) by calibration solutions prepared from the pure (isolated) compound with known purity or (ii) by approximation of the relative response factor via the effective carbon number (ECN) concept. Before analysis of the reaction mixture by GC/FID, a derivatisation treatment via trimethylsilylation (with N-methyl-N-(trimethylsilyl)trifluoroacetamide) was performed to enhance the volatility of the reaction products.

All zeolites having two or three interconnected and non-parallel channel systems, with a least one of said systems comprising 10- or more-membered ring channels and a framework $Si/Al_2$ ratio of at least 24, and all zeolites having three interconnected and non-parallel channel systems, with at least two of said channel systems comprising 10- or more membered ring channels and a framework $Si/Al_2$ ratio of at least 12, provided GGP yields above 14%, up to about 28%.

The results of the various experiments are summarized in Table 1. It is noted that for some zeolites, the framework $Si/Al_2$ ratio, may differ from the bulk $Si/Al_2$ ratio. For all zeolites, the framework $Si/Al_2$ ratio is provided, as this is the most relevant ratio for the catalysis. For some zeolites, the bulk $Si/Al_2$ ratio is also provided (between brackets).

Figure 2:
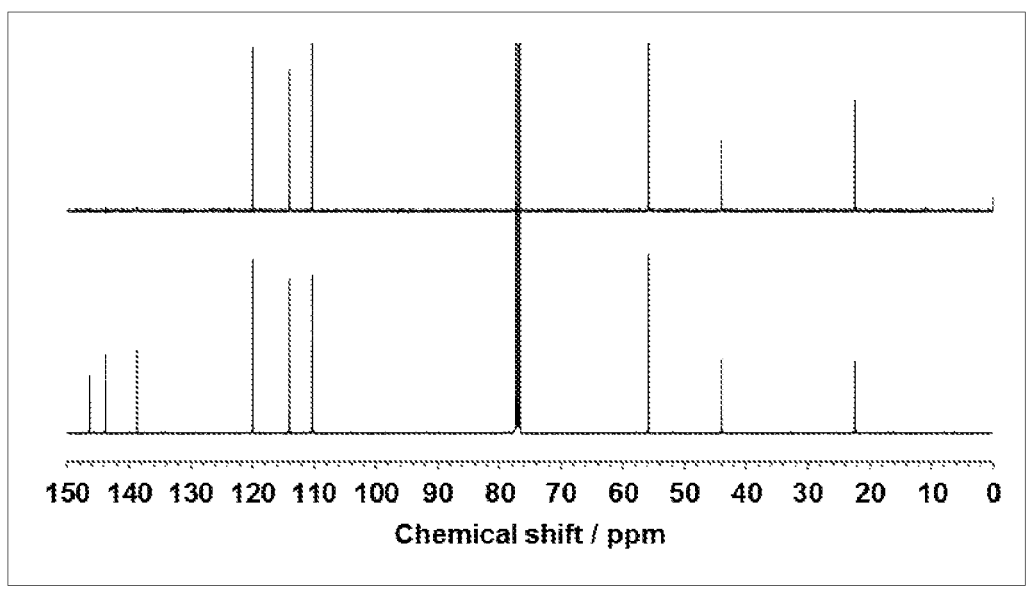
FIG. 2 shows representative $^{13}$C (bottom) and $^{13}$C-DEPT135 (top) NMR spectra of GGE monomer prepared according to the present invention.
Figure 3:
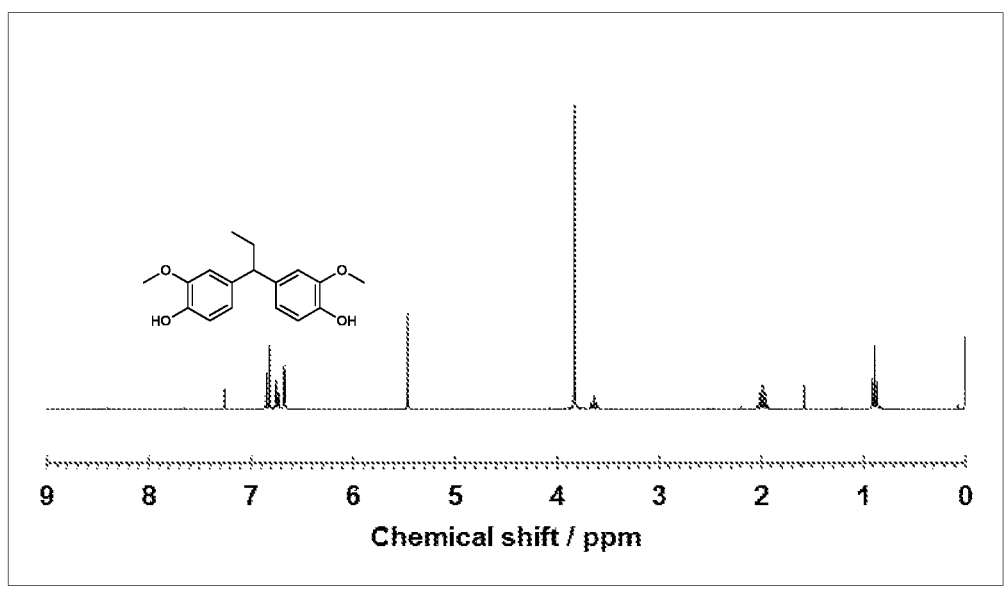
FIG. 3 shows a representative $^1$H NMR spectrum of GGP monomer prepared according to the present invention.
Figure 4:
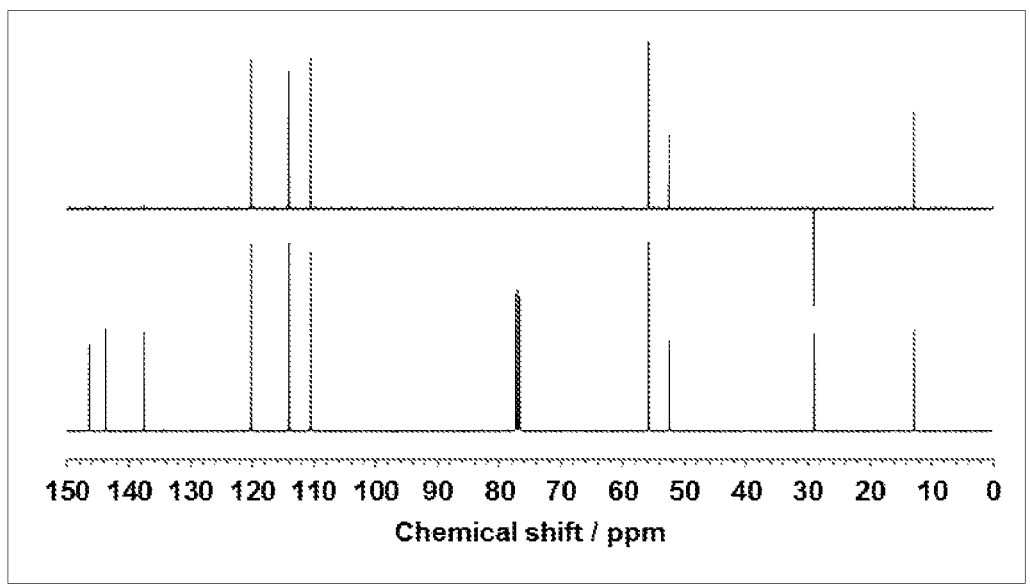
FIG. 4 shows representative $^{13}$C (bottom) and $^{13}$C-DEPT135 (top) NMR spectra of GGP monomer prepared according to the present invention.
Figure 5:
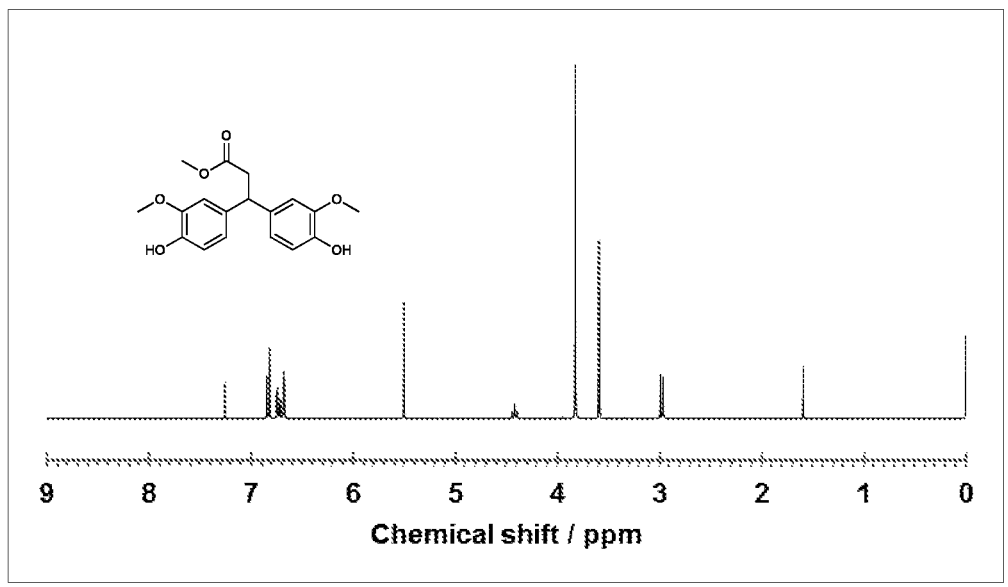
FIG. 5 shows a representative $^1$H NMR spectrum of GGPesterM monomer prepared according to the present invention.
Figure 6:
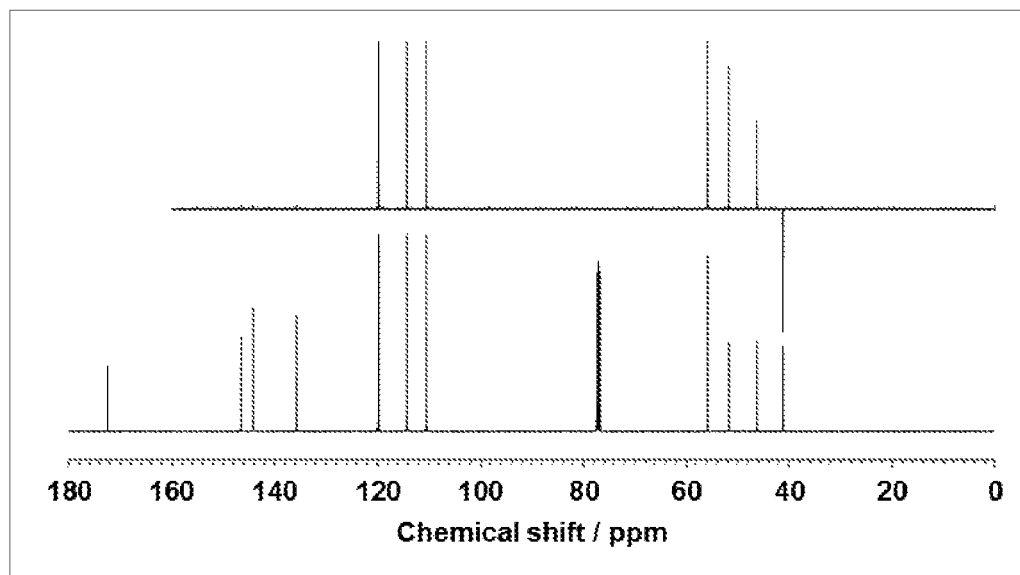
FIG. 6 shows representative $^{13}$C (bottom) and $^{13}$C-DEPT135 (top) NMR spectra of GGPesterM monomer prepared according to the present invention.
Figure 7:
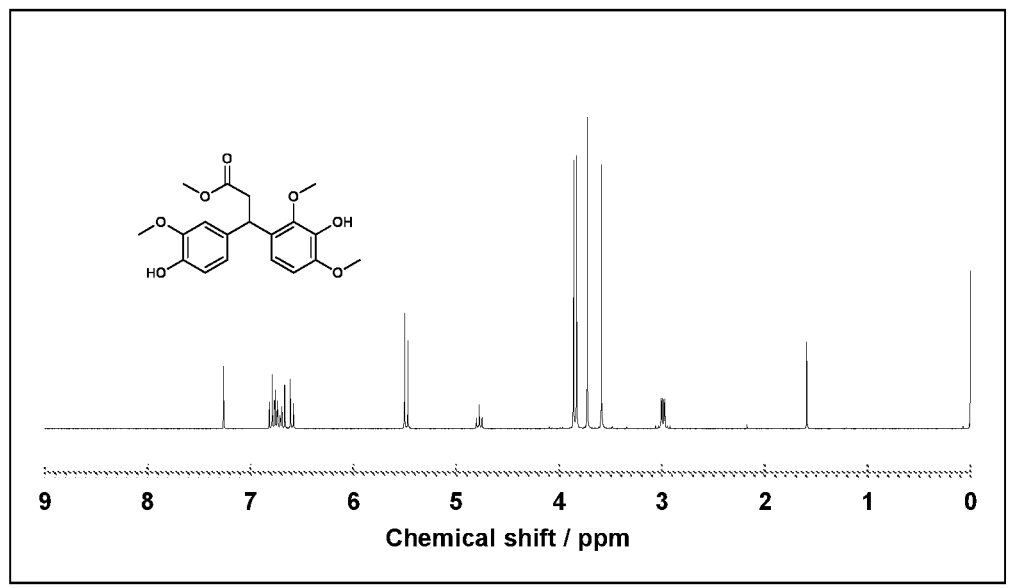
FIG. 7 shows a representative $^1$H NMR spectrum of GSPesterM monomer prepared according to the present invention.
Figure 8:
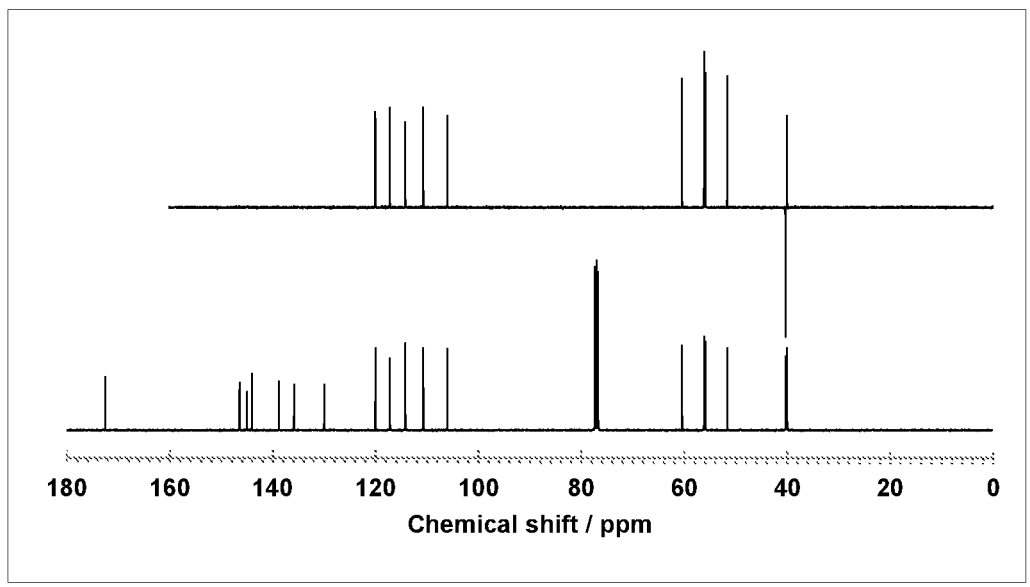
FIG. 8 shows representative $^{13}$C (bottom) and $^{13}$C-DEPT135 (top) NMR spectra of GSPesterM monomer prepared according to the present invention.
Figure 9:
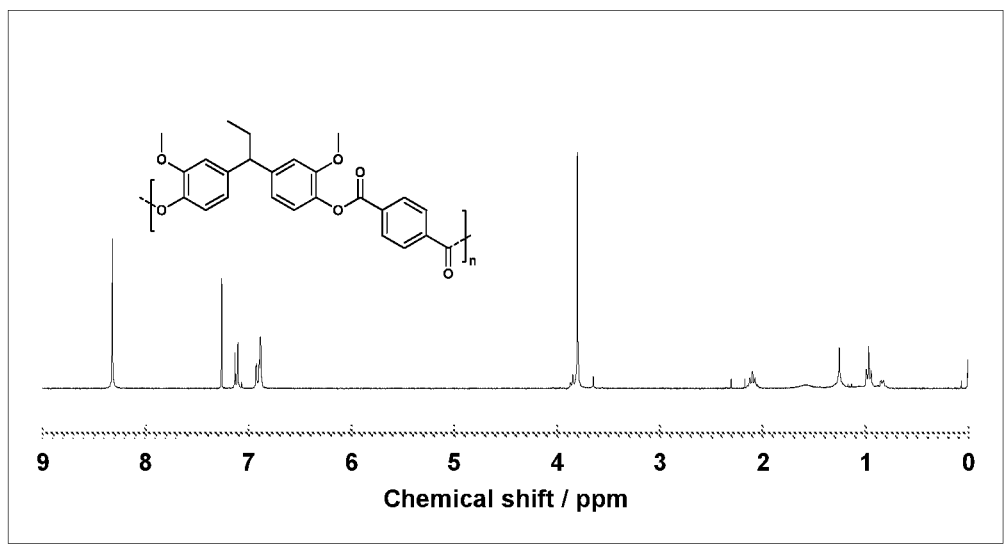
FIG. 9 shows a representative $^1$H NMR spectrum of poly(GGP-terephthalate) prepared according to the present invention.
Figure 10:
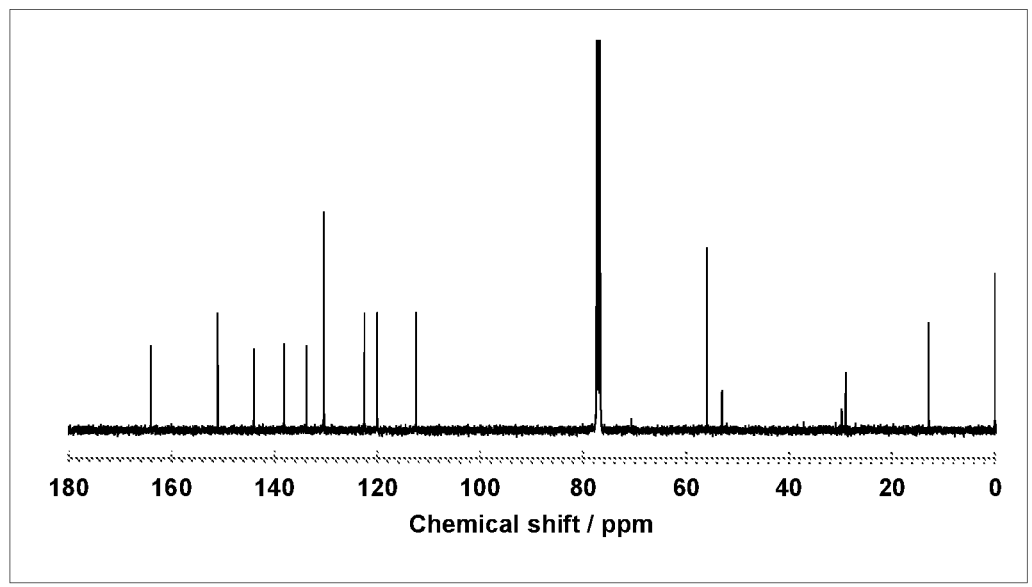
FIG. 10 shows a representative $^{13}$C NMR spectra of poly(GGP-terephthalate) prepared according to the present invention.

FIG. 2A shows the rate of GGP production per acid site (as calculated from the $Si/Al_2$ ratio) per hour for H-BEA and H-CBV zeolites, with varying $Si/Al_2$ ratios. For the all zeolites except . . . , the rate was calculated taking into account the amount of bisphenol formed after 2 hours. For the H-N Effect of Continuous Addition

TABLE 1

| Catalyst designation | Zeolite Topology | Zeolite Ring size | Number of interconnected non parallel channel systems | $Si/Al_2$ framework ratio | IE conversion (%) | GGP yield (%) | Dimer yield (%) | (pp' + mp')/op' | GGP/dimer |
| --- | --- | --- | --- | --- | --- | --- | --- | --- | --- |
| H-ZSM 5 | MFI | 10-10 | two systems with 10-membered ring channels | 30 | 15.1 | 0.9 | 6.3 | 10.0 | 0.1 |
| H-MOR | MOR | 12-8 | channel systems not interconnected (parallel channel system with 12- and 8-membered rings) | 200 | | | | | |
| H-BEA | BEA | 12-12-12 | three systems with 12-membered ring channels | 25 | 46.2 | 7.5 | 19.9 | 10.4 | 0.4 |
| H-BEA | BEA | 12-12-12 | three systems with 12-membered ring channels | 38 | 87.3 | 14.2 | 40.4 | 17.2 | 0.4 |
| H-BEA | BEA | 12-12-12 | three systems with 12-membered ring channels | 150 | 99.7 | 20.9 | 44.7 | 14.4 | 0.5 |
| H-BEA | BEA | 12-12-12 | three systems with 12-membered ring channels | 255 | 99.8 | 17.7 | 44.8 | 13.4 | 0.4 |
| H-CBV300 | FAU | 12-12-12 | three systems with 12-membered ring channels | 5.1 | <1 | 0.3 | 0.3 | n.a. | 1.0 |
| H-CBV500 | FAU | 12-12-12 | three systems with 12-membered ring channels | 5.2 | <1 | 0.1 | 0.2 | n.a. | 0.8 |
| H-CBV712 | FAU | 12-12-12 | three systems with 12-membered ring channels | 12 | 14.0 | 3.6 | 5.1 | 22.8 | 0.7 |
| H-CBV720 | FAU | 12-12-12 | three systems with 12-membered ring channels | 30 | >99.9 | 28.0 | 39.9 | 28.2 | 0.7 |
| H-CBV760 | FAU | 12-12-12 | three systems with 12-membered ring channels | 60 | >99.9 | 24.4 | 42.9 | 29.3 | 0.6 |
| H-CBV780 | FAU | 12-12-12 | three systems with 12-membered ring channels | 80 | >99.9 | 25.6 | 44.8 | 29.3 | 0.6 |
| $H_2SO_4$ | n.a. | n.a. | n.a. | n.a. | >99.9 | 24.4 | 41.7 | 14.1 | 0.6 |
| pTSA•$H_2O$ | n.a. | n.a. | n.a. | n.a. | >99.9 | 28.3 | 35.7 | 11.5 | 0.8 |
| Amberlyst-15 | n.a. | n.a. | n.a. | n.a. | 83.9 | 24.2 | 17.6 | 20.1 | 1.4 |
| No catalyst | n.a. | n.a. | n.a. | n.a. | | | | | | n.a.: not applicable

Example 2—Preparation of symmetric ortho methoxy p,p'-bisphenols 4,4'-(ethane-1,1-diyl)bis(2-methoxyphenol): GGE 7.60 g (60 mmol) 2-methoxyphenol (Sigma-Aldrich, 98%) and 60 mg (0.3 mmol) Amberlyst® 15 (Sigma-Aldrich, 5 mmol $H^+$/g, dry ≤1.5 wt %) were placed in a 10 mL round-bottom flask. The vessel was heated to 80° C. under air and continuous magnetic stirring (750 rpm). At reaction temperature, 0.23 g (1.5 mmol) 4-ethenyl-2-methoxyphenol (J&K Scientific, 98%) was gradually introduced via a Perfusor® Space Syringe Pump (B Braun) over 4 hours and stirred for an additional hour. The normalized addition factor for this semi-batch configuration was 0.021.

After the reaction, the hot reaction mixture was filtered and excess unreacted 2-methoxyphenol removed via vacuum distillation (90° C. at 20 mbar). The solid GGE product was characterized by GC(-MS), FTIR and $^1$H and $^{13}$C NMR. A full conversion of 4-ethenyl-2-methoxyphenol was achieved yielding 63.5 wt % GGE (81% p,p'-, 18% m,p'-isomer). Small white crystals of p,p'-GGE were grown from hot heptane and/or from slow evaporation of an diethyl ether/heptane solution at room temperature (isolated yield: 0.20 g, 48%).

5.07 g (40 mmol) 2-methoxyphenol (Sigma-Aldrich, 98%) and 0.46 g (0.1 mmol) H-BEA (Sid-Chemie, Si/Al$_2$ ratio of 150) were placed in a 10 mL round-bottom flask. The vessel was heated to 80° C. under air and continuous magnetic stirring (375 rpm). At reaction temperature, 0.31 g (2 mmol) 4-ethenyl-2-methoxyphenol (J&K Scientific, 98%) was gradually introduced via a Perfusor® Space Syringe Pump (B Braun) over 2 hours and stirred for an additional 30 minutes. The normalized addition factor for this semi-batch configuration was 0.25. After the reaction, the hot reaction mixture was filtered and excess unreacted 2-methoxyphenol removed via vacuum distillation (90° C. at 20 mbar). The solid GGE product was characterized by GC(-MS), FTIR and $^1$H and $^{13}$C NMR. A full conversion of 4-ethenyl-2-methoxyphenol was achieved yielding 70.1 wt % GGE (77% p,p'-, 21% m,p'-isomer). Small white crystals of p,p'-GGE were grown from hot heptane and/or from slow evaporation of an diethyl ether/heptane solution at room temperature (isolated yield: 0.28 g, 51%)

M.p. 105-107° C.; $^1$H NMR (300 MHz, CDCl$_3$, 25° C., TMS): $\delta_H$=1.58 (d, $^3$J(H,H)=7.2 Hz, 3H; —CHCH$_3$), 3.82 (s, 6H; —OCH$_3$), 4.01 (q, $^3$J(H,H)=7.2 Hz, 1H; —CHCH$_3$), 5.48 (s, 2H; —ArOH), 6.67 (d, $^4$J(H,H)=1.9 Hz, 2H; -m-ArH), 6.73 (dd, $^3$J(H,H)=8.1, $^4$J(H,H)=1.9 Hz, 2H; -m-ArH), 6.84 ppm (d, $^3$J(H,H)=8.1 Hz, 2H; -o-ArH); $^{13}$C NMR (100 MHz, CDCl$_3$, 25° C., TMS): $\delta_c$=146.3, 143.8, 138.7, 119.9, 114.0, 110.3, 55.9, 44.0, 22.4 ppm; MS (70 eV, EI): m/z (%): 274 (31) [M$^{+•}$], 259 (100) [M$^{+•}$-$^•$CH$_3$], 229 (8)

4,4'-(propane-1,1-diyl)bis(2-methoxyphenol): GGP 7.60 g (60 mmol) 2-methoxyphenol (Sigma-Aldrich, 98%) and 60 mg (0.3 mmol) Amberlyst® 15 (Sigma-Aldrich, 5 mmol H$^+$/g, dry ≤1.5 wt %) were placed in a 10 mL round-bottom flask. The vessel was heated to 80° C. under air and continuous magnetic stirring (750 rpm). At reaction temperature, 0.25 g (1.5 mmol) 2-methoxy-4-(prop-1-en-1-yl)phenol (Sigma-Aldrich, 99%, mixture of cis and trans) was gradually introduced via a Perfusor® Space Syringe Pump (B Braun) over 4 hours and stirred for an additional hour. The normalized addition factor for this semi-batch configuration was 0.021. After the reaction, the hot reaction mixture was filtered and excess unreacted 2-methoxyphenol removed via vacuum distillation (90° C. at 20 mbar). The solid GGP product was characterized by GC(-MS), FTIR and $^1$H and $^{13}$C NMR. A full conversion of 2-methoxy-4-(prop-1-en-1-yl)phenol was achieved yielding 77.9 wt % GGP (82% p,p'-, 17% m,p'-isomer). Highly pure transparent crystals of p,p'-GGP were grown from hot heptane and/or slow evaporation of an acetone/heptane solution at room temperature (isolated yield: 0.26 g, 60%).

5.07 g (40 mmol) 2-methoxyphenol (Sigma-Aldrich, 98%) and 0.25 g (0.1 mmol) H-CBV780 (Zeolyst, Si/Al$_2$ ratio of 80) were placed in a 10 mL round-bottom flask. The vessel was heated to 80° C. under air and continuous magnetic stirring (375 rpm). At reaction temperature, 0.33 g (2 mmol) 2-methoxy-4-(prop-1-en-1-yl)phenol (Sigma-Aldrich, 99%, mixture of cis and trans) was gradually introduced via a Perfusor® Space Syringe Pump (B Braun) over 2 hours and stirred for an additional 30 minutes. The normalized addition factor for this semi-batch configuration was 0.25. After the reaction, the hot reaction mixture was filtered and excess unreacted 2-methoxyphenol removed via vacuum distillation (90° C. at 20 mbar). The solid GGP product was characterized by GC(-MS), FTIR and $^1$H and $^{13}$C NMR. A full conversion of 2-methoxy-4-(prop-1-en-1-yl)phenol was achieved yielding 79.8 wt % GGP (82% p,p'-, 17% m,p'-isomer). Highly pure transparent crystals of p,p'-GGP were grown from hot heptane and/or slow evaporation of an acetone/heptane solution at room temperature (isolated yield: 0.36 g, 63%).

M.p. 119-120 OC; $^1$H NMR (300 MHz, CDCl$_3$, 25° C., TMS): $\delta$=0.89 (t, $^3$J(H,H)=7.3 Hz, 3H; —CH$_2$CH$_3$), 1.98 (quin, $^3$J(H,H)=7.3 Hz, 2H; —CHCH$_2$CH$_3$), 3.64 (t, $^3$J(H,H)=7.5 Hz, 1H; —CHCH$_2$), 3.83 (s, 6H; —OCH$_3$), 5.47 (s, 2H; —ArOH), 6.67 (d, $^4$J(H,H)=1.9 Hz, 2H; -m-ArH), 6.74 (dd, $^3$J(H,H)=8.1, $^4$J(H,H)=1.9 Hz, 2H; -m-ArH), 6.84 ppm (d, $^3$J(H,H)=8.1 Hz, 2H; -o-ArH); $^{13}$C NMR (100 MHz, CDCl$_3$, 25° C., TMS): $\delta$=146.4, 143.8, 137.5, 120.2, 114.1, 110.5, 55.8, 52.5, 29.0, 12.8 ppm; MS (70 eV, EI): m/z (%): 288 (15) [M$^{+•}$], 259 (100) [M$^{+•}$-$^•$CH$_3$], 229 (8)

methyl 3,3-bis(4-hydroxy-3-methoxyphenyl)propanoate: GGPesterM 2.53 g (20 mmol) 2-methoxyphenol (Sigma-Aldrich, 98%) and 0.21 g (1 mmol) methyl 3-(4-hydroxy-3-methoxyphenyl)prop-2-enoate (Alfa Aesar, 99%, predominantly trans) were placed in a 10 mL round-bottom flask. The vessel was heated to 100° C. under continuous magnetic stirring. At reaction temperature, 20 mg (0.1 mmol) Amberlyst® 15 (Sigma-Aldrich, 5 mmol H$^+$/g, dry ≤1.5 wt %) was quantitatively introduced (cf. batch operation). After 4 hours of reaction, the hot reaction mixture was filtered and excess unreacted 2-methoxyphenol removed via vacuum distillation (90° C. at 20 mbar). The solid GGPesterM product was characterized by GC(-MS), FTIR and $^1$H and $^{13}$C NMR. A full conversion of methyl 3-(4-hydroxy-3-methoxyphenyl)prop-2-enoate was achieved yielding 91.6 wt % GGPesterM (78% p,p'-isomer, 20% m,p'-isomer). Highly pure transparent crystals of p,p'-GGPesterM were grown from hot heptane and/or slow evaporation of an acetone/heptane solution at room temperature (isolated yield: 0.24 g, 71%).

5.07 g (40 mmol) 2-methoxyphenol (Sigma-Aldrich, 98%) and 0.42 g (2 mmol) methyl 3-(4-hydroxy-3-methoxyphenyl)prop-2-enoate (Alfa Aesar, 99%, predominantly trans) were placed in a 10 mL round-bottom flask. The vessel was heated to 80° C. under continuous magnetic stirring (375 rpm). At reaction temperature, 0.25 g (0.1 mmol) H-CBV780 (Zeolyst, Si/Al$_2$ ratio of 80) was quantitatively introduced (cf batch operation). After 2.5 hours of reaction, the hot reaction mixture was filtered and excess unreacted 2-methoxyphenol removed via vacuum distillation (90° C. at 20 mbar). The solid GGPesterM product was characterized by GC(-MS), FTIR and $^1$H and $^{13}$C NMR. A full conversion of methyl 3-(4-hydroxy-3-methoxyphenyl)prop-2-enoate was achieved yielding 93.4 wt % GGPesterM (81% p,p'-, 18% m,p'-isomer). Highly pure transparent crystals of p,p'-GGPesterM were grown from hot heptane and/or slow evaporation of an acetone/heptane solution at room temperature (isolated yield: 0.49 g, 73%).

M.p. 116-120° C.; $^1$H NMR (300 MHz, CDCl$_3$, 25° C., TMS): $\delta$=2.98 (d, $^3$J(H,H)=8.0 Hz, 2H; —CHCH$_2$(CO)—), 3.59 (s, 3H; —(CO)OCH$_3$), 3.82 (s, 6H; —OCH$_3$), 4.42 (t, $^3$J(H,H)=8.0 Hz, 1H; —CHCH$_2$), 5.51 (s, 2H; —ArOH), 6.68 (d, $^4$J(H,H)=2.0 Hz, 2H; -m-ArH), 6.73 (dd, $^3$J(H,H)= 8.1, $^4$J(H,H)=1.9 Hz, 2H; -m-ArH), 6.83 ppm (d, $^3$J(H,H)= 8.1 Hz, 2H; -o-ArH); $^{13}$C NMR (100 MHz, CDCl$_3$, 25° C., TMS): δ=172.5, 146.5, 144.2, 135.7, 119.9, 114.3, 110.5, 55.8, 51.7, 46.3, 41.2 ppm; MS (70 eV, EI): m/z (%): 332 (26) [M$^{+•}$], 259 (100) [M$^{+•}$-$^•$CH$_2$(CO)OCH$_3$], 229 (6)

Example 3—Preparation of Polyesters from Symmetric Ortho Methoxy p,p'-Bisphenols 0.2307 g (0.8 mmol) 4,4'-(propane-1,1-diyl)bis(2-methoxyphenol) (>99.5%) was dissolved in 1.7 mL of 1 M aqueous solution of sodium hydroxide (Fisher Scientific, 98.9%) in a 10 mL round bottom flask equipped with a mechanical stirrer. The mixture was stirred for 30 min at 10° C. Next, 9.3 mg (41 µmol) benzyltriethylammonium chloride (Sigma-Aldrich, 99%) was added to the reaction mixture and stirring was continued at 10° C. After 30 min, a solution of 0.1624 g (0.8 mmol) terephthaloyl chloride (Sigma-Aldrich, ≥99%) in 5 mL of dichloromethane was added to the reaction mixture and the mixture was stirred vigorously (2000 rpm). After 1 h of reaction at 10° C., the reaction mixture was poured into hot water (50° C., 150 mL); the precipitated polymer was filtered and washed with water (3×50 mL). The polymer was dissolved in chloroform and reprecipitated into ice-cooled methanol (150 mL). The polymer was filtered, washed with ice-cooled methanol (3×50 mL), and dried in vacuo (25° C., ~2 mbar) until constant weight was reached.

Yield: 0.3348 g (96%); $^1$H NMR (300 MHz, CDCl$_3$, 25° C., TMS): δ=0.97 (t, $^3$J(H,H)=7.3 Hz, 3H; —CH$_2$CH$_3$), 2.10 (quin, $^3$J(H,H)=7.3 Hz, 2H; —CHCH$_2$CH$_3$), 3.80 (s, 6H; —OCH$_3$), 3.85 (t, $^3$J(H,H)=7.3 Hz, 1H; —CHCH$_2$), 6.88 (d, $^4$J(H,H)=1.9 Hz, 2H; -m-ArH), 6.91 (dd, $^3$J(H,H)=8.1, $^4$J(H,H)=1.9 Hz, 2H; -m-ArH), 7.12 (d, $^3$J(H,H)=8.1 Hz, 2H; -o-ArH), 8.32 ppm (s, 4H; —ArH); $^{13}$C NMR (100 MHz, CDCl$_3$, 25° C., TMS): δ=164.0, 151.0, 143.9, 138.1, 133.7, 130.4, 122.5, 120.0, 112.5, 55.9, 53.0, 29.0, 12.8 ppm; Molecular weight (GPC in THF, 30° C., 254 nm, PS standards): M$_n$=32000 and M$_w$=132000 g·mol$^{-1}$, PDI=4.1

The invention claimed is:
1. A process for preparing a compound, comprising:
 a. contacting at least one (alk-1-enyl)alkoxyphenol; wherein said (alk-1-enyl)alkoxyphenol is an 3-(alk-1-enyl)alkoxyphenol, an 4-(alk-1-enyl)alkoxyphenol, an 5-(alk-1-enyl)alkoxyphenol or an 6-(alk -1-enyl)alkoxyphenol, comprising the formula (I):

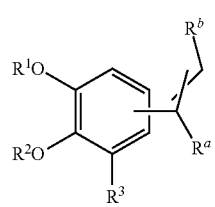

(I)

wherein if R$^1$ is hydrogen (—H) then R$^2$ is independently methyl (—CH$_3$) or ethyl (—CH$_2$CH$_3$); and R$^3$ is independently hydrogen (—H), hydroxy (—OH), methoxy (—OCH$_3$) or ethoxy (—OCH$_2$CH$_3$); and
wherein if R$^2$ is hydrogen (—H) then R$^1$ is independently methyl (—CH$_3$) or ethyl (—CH$_2$CH$_3$); and R$^3$ is independently hydroxy (—OH), methoxy (—OCH$_3$) or ethoxy (—OCH$_2$CH$_3$); and
wherein R$^a$ is independently hydrogen (—H), methyl (—CH$_3$) or ethyl (—CH$_2$CH$_3$); and R$^b$ is independently hydrogen (—H), methyl (—CH$_3$), ethyl (—CH$_2$CH$_3$), hydroxymethyl (—CH$_2$OH), methoxymethyl (—CH$_2$OCH$_3$), methyl carboxylate (—CH$_2$O(CO)R), carboxymethyl (—CH$_2$(CO)OH) or an ester (—CH$_2$(CO)OR), an amide (—CH$_2$CONHR) or salt thereof;

b. contacting at least one alkoxyphenol; wherein said alkoxyphenol is a 2-alkoxyphenol, a 3-alkoxyphenol, a 2,3-dialkoxyphenol, or a 2,6-dialkoxyphenol comprising the formula (II):

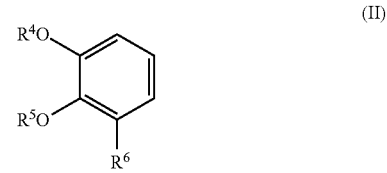

(II)

wherein if R$^4$ is hydrogen (—H) then R$^5$ is independently methyl (—CH$_3$) or ethyl (—CH$_2$CH$_3$); and R$^6$ is independently hydrogen (—H), hydroxy (—OH), methoxy (—OCH$_3$) or ethoxy (—OCH$_2$CH$_3$);
wherein if R$^5$ is hydrogen (—H) then R$^4$ is independently methyl (—CH$_3$) or ethyl (—CH$_2$CH$_3$); and R$^6$ is independently hydroxy (—OH), methoxy (—OCH$_3$) or ethoxy (—OCH$_2$CH$_3$);

with at least one acidic catalyst; wherein said acidic catalyst comprises an acid selected of the group consisting of a soluble acid, an acidic ion-exchange resin, an acidic clay and an acidic zeolite; and wherein said compound is an ortho alkoxy bisphenol monomer of formula (III):

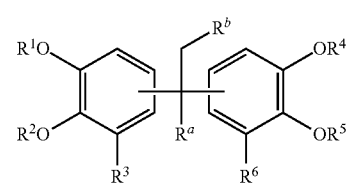

(III)

wherein R$^1$-R$^6$, R$^a$ and R$^b$ are as defined herein for formula (I) and formula (II); and
wherein the bridging carbon group, connecting the two hydroxyl-substituted aryl groups, and the hydroxyl substituent (next to the alkoxy) on each aryl group are disposed ortho, meta or para to each other on the aryl group bearing the phenolic (—ArOH) functionality.

2. The process for preparing a compounds according to claim 1, comprising:
 a. contacting at least one (alk-1-enyl)alkoxyphenol; wherein said (alk-1-enyl)alkoxyphenol is an 3-(alk-1-enyl)alkoxyphenol, an 4-(alk-1-enyl)alkoxyphenol, an 5-(alk-1-enyl)alkoxyphenol or an 6-(alk -1-enyl) alkoxyphenol, comprising the formula (I):

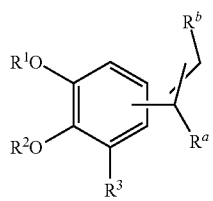

(I)

wherein if R¹ is hydrogen (—H) then R² is independently methyl (—CH₃) or ethyl (—CH₂CH₃); and R³ is independently hydrogen (—H), hydroxy (—OH), methoxy (—OCH₃) or ethoxy (—OCH₂CH₃); and wherein if R² is hydrogen (—H) thenthan R¹ is independently methyl (—CH₃) or ethyl (—CH₂CH₃); and R³ is independently hydroxy (—OH), methoxy (—OCH₃) or ethoxy (—OCH₂CH₃); and wherein Ra is independently hydrogen (—H), methyl (—CH₃) or ethyl (—CH₂CH₃); and $R^b$ is independently hydrogen (—H), methyl (—CH₃), ethyl (—CH₂CH₃), hydroxymethyl (—CH₂OH), methoxymethyl (—CH₂OCH₃), methyl carboxylate (—CH₂O(CO)R), carboxymethyl (—CH₂(CO)OH) or an ester (—CH₂(CO)OR), an amide (—CH₂CONHR) or salt thereof;

b. contacting at least one alkoxyphenol; wherein said alkoxyphenol is a 2-alkoxyphenol, a 3-alkoxyphenol, a 2,3-dialkoxyphenol, or a 2,6-dialkoxyphenol comprising the formula (II):

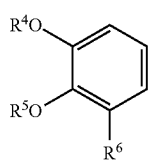

(II)

wherein if R⁴ is hydrogen (—H) then R⁵ is independently methyl (—CH₃) or ethyl (—CH₂CH₃); and R⁶ is independently hydrogen (—H), hydroxy (—OH), methoxy (—OCH₃) or ethoxy (-OCH₂CH₃);

wherein if R⁵ is hydrogen (—H) then R⁴ is independently methyl (—CH₃) or ethyl (—CH₂CH₃); and R⁶ is independently hydroxy (—OH), methoxy (—OCH₃) or ethoxy (—OCH₂CH₃);

with at least one acidic catalyst; wherein said acidic catalyst comprises an acid selected of the group consisting of a soluble acid, an acidic ion-exchange resin, an acidic clay and an acidic zeolite; and wherein said compounds comprise asymmetric and symmetric ortho alkoxy bisphenol monomers of formula (III):

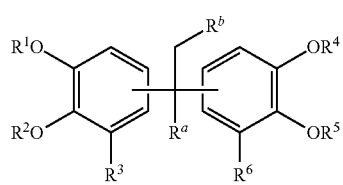

(III)

wherein R¹-R⁶, $R^a$ and $R^b$ are as defined herein for formula (I) and formula (II); and wherein the bridging carbon group, connecting the two hydroxyl-substituted aryl groups, and the hydroxyl substituent (next to the alkoxy) on each aryl group are disposed ortho, meta or para to each other on the aryl group bearing the phenolic (—ArOH) functionality.

3. The process according to claim 1, wherein the acidic catalyst is an acidic zeolite.

4. The process according to claim 1, wherein said at least one (alk-1-enyl)alkoxyphenol is selected from the group comprising 4-vinylguaiacol, 4-vinylguaethol, 3-methoxy-5-vinylcatechol and 4-vinylsyringol.

5. The process according to claim 1, wherein said at least one (alk-1-enyl)alkoxyphenol is selected from the group comprising isoeugenol, propenylguaethol, 3-methoxy-5-(prop-1-en-1-yl)catechol, and 4-(prop-1-en-1-yl)syringol.

6. The process according to claim 1, wherein said at least one (alk-1-enyl)alkoxyphenol is selected from the group comprising coniferyl alcohol, 5-hydroxyconiferyl alcohol and sinapyl alcohol; and an ether or ester thereof.

7. The process according to claim 1, wherein said at least one (alk-1-enyl)alkoxyphenol is selected from the group comprising isoferulic acid, ferulic acid, 5-hydroxyferulic acid and sinapic acid; and an ester, an amide, or salt thereof.

8. The process according to claim 1, wherein said at least one alkoxyphenol is selected from the group comprising guaiacol, 3-methoxycatechol, 2-methoxyresorcinol, 2,3-dimethoxyphenol and syringol.

9. The process according to claim 1, wherein said at least one alkoxyphenol is selected from the group comprising guaethol, 3-ethoxycatechol, 2-ethoxyresorcinol, 2,3-diethoxyphenol and 2,6-diethoxyphenol.

10. The process according to claim 1, wherein said at least one acidic catalyst is a anhydrous Brønsted acidic catalyst.

11. The process according to claim 1, wherein said at least one soluble acid is selected from the group comprising acidic hydracids, oxyacids, sulfonic acids and fluorosulfonic acids.

12. The process according to claim 1, wherein said at least one acidic ion-exchange resin comprises acidic sulfonated ion-exchange resins.

13. The process according to claim 1, wherein said at least one acidic clay comprises a acidic clay comprising montmorillonite or bentonite.

14. The process according to claim 1, wherein said at least one acidic zeolite comprises:

two or three interconnected and non-parallel channel systems, wherein at least one of said channel systems comprises 10- or more-membered ring channels; and a framework Si/X₂ ratio of at least 24 as measured by NMR; or three interconnected and non-parallel channel systems, wherein at least two of said channel systems comprise 10- or more-membered ring channels; and a framework Si/X₂ ratio of at least 12 as measured by NMR;

wherein each X is Al or B.

15. The process according to claim 14, wherein at least one of said interconnected and non-parallel channel systems comprises 12- or more membered ring channels.

16. The process according to claim 14, wherein X is Al.

17. The process according to claim 1, wherein said acidic catalyst has a Brønsted acid density between 0.05 and 6.5 mmol/g dry weight.

18. The process according to claim 1, wherein said acidic zeolite comprises a BEA topology, a MFI topology, a FAU topology, a MEL topology, a FER topology, or a MWW topology.

19. The process according to claim 1, wherein said acidic zeolite comprises a FAU topology.

20. The process according to claim 1, wherein said acidic zeolite comprises at least three interconnecting and non-parallel channel systems.

21. The process to claim 1, wherein said (alk-1-enyl) alkoxyphenol is provided in a composition comprising said (alk-1-enyl)alkoxyphenol in a concentration of a least 0.01 wt % based on a total weight of the composition.

22. The process to claim 1, wherein said (alk-1-enyl) alkoxyphenol and alkoxyphenol are at least 1 wt % derived from bio-based material.

23. The process according to claim 22, wherein said bio-based material comprises plant material, bio based oil, biorefinery waste, or a combination thereof.

24. The process according to claim 23, wherein said plant material comprises at least one lignocellulosic material and/or said bio-based oil comprises pyrolysis oil.

25. The process according to claim 1, further comprising converting said ortho alkoxy bisphenol monomers to polymers.

26. The method according to claim 25, wherein said polymers are thermoplastics or thermosetting resins.

27. The method according to claim 26, wherein said thermoplastics are polycarbonates, produced by reaction of said ortho alkoxy bisphenol monomers with a carbonate source selected from the group consisting of cyclic carbonates, dialkyl carbonates, diaryl carbonates, chloroformates, p-nitrophenyl chloroformate, phosgene, diphosgene, triphosgene (BTC), N,N '-carbonyldiimidazole (CDI), disuccinimidyl carbonate (DSC), and bis(2-pyridyl) carbonate.

28. The method according to claim 25, wherein said polymers are polycarbonates (PC), polyiminocarbonates (PIC), polyesters (PE), polyester-styrenes, polyurethanes, polyarylates, polyethers, polysulfones (PSU), polyarylsulfones, polyethersulfones (PESU), polyarylethersulfone (PAES), polyetheretherketones (PEEK), polyaryletherketones (PAEK), polyacetals, polyketones, alkylphenolic polymers, polyoxalates, polyalylates, epoxy resins, phenolic resins, vinyl ester resins, polyphenylene ether resins, polyphenylene sulphide resins, polyetherimide resins, cyanate ester resins, benzoxazine resins, bismaleimide resins and other end-capped resins and any combination thereof.

29. The method according to claim 26, wherein said thermoplastics are polyesters, produced by reaction of said ortho alkoxy bisphenol monomers with a saturated or unsaturated aliphatic diacid, or derivatives thereof, selected from the group consisting of oxalic acid, malonic acid, maleic acid, fumaric acid, succinic acid, adipic acid, muconic acid, citraconic, mesaconic and itaconic acid, and/or anhydrides, $C_{1-6}$alkyl esters, $C_{6-10}$aryl esters and/or acid chlorides thereof.

30. The method according to claim 26, wherein said thermoplastics are polyesters, produced by reaction of said ortho alkoxy bisphenol monomers with derivatives of aromatic dicarboxylic acids selected from the group consisting of phthalic acid, isophthalic acid, terephthalic acid, 2,5-furandicarboxylic acid, and corresponding thiophene or 1H-pyrrole analogues, and/or anhydrides, $C_{1-6}$alkyl esters, $C_{6-10}$aryl esters and/or acid chlorides thereof.

* * * * *